(12) United States Patent
Johnston et al.

(10) Patent No.: US 6,670,479 B2
(45) Date of Patent: Dec. 30, 2003

(54) AMINATION PROCESS

(75) Inventors: Jeffrey N. Johnston, Bloomington, IN (US); Rajesh Viswanathan, Bloomington, IN (US)

(73) Assignee: Advanced Research and Technology Institute, Inc., Bloomington, IN (US)

( * ) Notice: Subject to any disclaimer, the term of this patent is extended or adjusted under 35 U.S.C. 154(b) by 148 days.

(21) Appl. No.: 09/801,269

(22) Filed: Mar. 7, 2001

(65) Prior Publication Data

US 2002/0128490 A1 Sep. 12, 2002

(51) Int. Cl.$^7$ ...................... C07D 213/04; C07D 213/06
(52) U.S. Cl. ...................... 546/329; 546/334; 546/268.1
(58) Field of Search ............................... 546/329, 334, 546/268.1

(56) References Cited

FOREIGN PATENT DOCUMENTS

WO          99/55723       * 11/1999    .................. 514/357

OTHER PUBLICATIONS

Giese, B., Kopping, B., et al., "Radical Cyclization Reactions", Organic Reactions, Paquette, L.A. Ed., Wiley: New York, 1996; vol. 48, Chap. 2.
Guichard, G., & Seebach, D., "Solid–Phase Synthesis of β–Oligopeptides", Chimia, 51, 1997, pp. 315–318.
Cordell, G.A., Ed., "The Alkaloids: Chemistry and Biology", Academic: San Diego, 1998, vol. 50.
Kent, S.B.H., "Chemical Synthesis of Peptides and Proteins", Ann. Rev. Biochem.., 1998, vol. 57, pp. 957–989.
Ryu, I., et al., "Nitrogen–philic Cyclization of Acyl Radicals Onto N═C Bond. New Synthesis of 2–Pyrrolidinones By Radical Carbonylation/Annulation Method", J. Am. Chem. Soc., 1998, 120, pp. 5838–5839.
Corey, E.J., et al., "A Rational Approach To Catalytic Enantioselective Enolate Alkylation Using A Structurally Ridgidified and Defined Chiral Quaternary Ammonium Salt Under Phase Transfer Conditions", J. Am. Chem. Soc., 1997, 119, pp. 12414–12415.
Kawase, M., et al., "Electrophilic Aromatic Substitution with N–Methoxy–N–acylnitrenium Ions Generated from N–Chloro–N–methoxyamides: Synthesis of Nitrogen Heterocyclic Compounds Bearing a N–Methoxyamide Group", J. Org. Chem., 1989, 54, pp. 3394–3403.
Hart, D.J. & Seely, F.L., "Bis(trimethylstannyl) benzopinacolate–Mediated Intermolecular Free–Radical Carbon–Carbon Bond–Forming Reactions: A New One–Carbon Homologation", J. Am. Chem.. Soc., 1988, 110, pp. 1631–1633.
Takeda, A., et al., "Palladium–Catalyzed [4+2] Cross–Benzannulation Reaction of Conjugated Enynes with Diynes and Triynes", J. Am. Chem. Soc., 1999, 121, pp. 6391–6402.

Fersht, A., "Structure and Mechanism in Protein Science: A Guide to Enzyme Catalysis and Protein Folding", W.H. Freeman and Company: New York, 1999.
Juaristi, E., Ed., "Enantioselective Synthesis of β–Amino Acids", Wiley–VCH: New York, 1997, pp. 139–149.
Creighton, T.E., "Proteins: Structures and Molecular Properties" $2^{nd}$ Ed., W.H. Freeman and Company: New York, 1993.
Bartlett, P.A. et al., "Radical Cyclization of Oxime Ethers", J. Am. Chem. Soc., 1988, 110, pp. 1633–1634.
Takano, S. et al. "Synthesis of Racemic Cryptostylines I, II and III by Radical Cyclization", Chemical Letters, 1990, pp. 315–316.
"Indoline Formation by Regioselective Aryl Radical Cyclization to Azomethine Bond," S. Takano, et al.; vol. 37, No. 1, 1994, Heterocycles, pp. 149–152.
"Cyclisation of Carbinyl Radicals onto Imines and Hydrazones," W.R. Bowman, et al.; vol. 35, Tetrahedron Letters, Elsevier Science Ltd., pp. 6369–6372.
"Rate Constants for Aryl Radical Cyclization to Aldimines: Synthesis of Tetrahydroisoquinolines by Fast 6–Endo Closures to Carbon," M.J. Tomaszewski, et al.; Pergamon Press Ltd., pp. 2123–2126.
"Total Synthesis of 26–Hydroxy–Epothilone B and Related Analogs via a Macrolactonization Based Strategy," K.C. Nicolaou, et al.; Tetrahedron 54 (1998).
"Synthesis of Racemic Cryptostylines I, II, and III by Radical Cyclization," S. Takano, et al., Chemistry Letters, The Chemical Society of Japan, 1990, pp. 315–316.
Wolfe, J.P.; Wagaw, S.; Marcoux, J–F.; Buchwald, S.F. Acc. Chem. Res. 1998, 31, 805.
López–Alvarado, P.; Avendaño, C.; Menendez, J.C. J.Org. Chem. 1995, 60, 5678.
Takeda, A.; Kamijo, S.; Yamamoto, Y. J. Am. Chem. Soc. 2000, 122, 5662.
Kobayashi, Y.; Fukuyama, T. J. Heterocycl. Chem. 1998, 35, 1043.
Kawase, M.; Kitamura, T.; Kikugawa, Y. J. Org. Chem. 1989, 54, 3394.
Wagaw, S.; Yang, B.H.; Buchwald, S.L. J. Am. Chem. Soc. 1999, 121, 10251.
Suehiro, T.; Suzuki, A.; Tsuchida, Y.; Yamazaki, J. Bull. Chem. Soc. Jpn. 1977, 50, 3324.
Chatgilialogu, C.; Crich, D. Komatsu, M.; Ryu, I. Chem. Rev. 1999, 99, 1991.

(List continued on next page.)

Primary Examiner—Charanjit S. Aulakh
(74) Attorney, Agent, or Firm—Kilpatrick Stockton LLP

(57) ABSTRACT

The present invention provides methodology for carbon-nitrogen bond formation via vinyl or aryl amination. In the process of the invention, an sp$^2$ hybridized radical is reacted with an azomethine moiety to form pyrrolidine and indole compounds. The methodology provides a facile process for the synthesis of compounds having the pyrrolidine or indole subunit and is especially advantageous for compounds having acid or base labile functional groups and/or is comprised of chiral centers susceptible to acid/base epimerization.

2 Claims, No Drawings

OTHER PUBLICATIONS

Greene, T.W.; Wuts, P. G. M. Protective Groups in Organic Synthesis 3$^{rd}$ Ed.; Wiley: NY, 1999, pp. 579–583.
Pangborn, A.B.; Giardello, M.A.; Grubbs, R.H.; Rosen, R.K.; Timmers, F.J. *Ogranometallics* 1996, 15, 1518–1520.
Wynberg et al. *J. Org. Chem.* 1993, 58, 5101.
Bunnett *Acc. Chem. Res.* 1978, 413.
Biehl & Razzuk *J. Org. Chem.* 1987, 52, 2619.
Mitchell et al., Azodicarboxylates: *J. Org. Chem.* 1994, 59, 682.
Nitrenium ions: *J. Org. Chem.* 1989, 54, 3394.
Barton et al. *Tetrahedron Lett.* 1986, 27, 3615.
Chan et al. *Tetrahedron Lett.* 1998, 39, 2933.
Hartwig, *Pure Appl. Chem.* 1999, 71, 1417.
McClure *Tetrahedron* 1998, 54, 7121.
Corey & Pyne *TL* 1983, 24, 2821.
Kim et al. *JACS* 1991, 113, 9882.
Buchwald et al. *J. Am. Chem. Soc.* 1997, 119, 8451.
Y. Ito et al. *J. Am. Chem. Soc.* 2000, 122, 7614.
O'Donnell et al. *J. Am. Chem. Soc.* 1989, 111, 2353.
Marks et al. *J. Am. Chem. Soc.* 1996, 118, 9295.
Stevens et al. *J. Am. Chem. Soc.* 1968, 5576.
Nowick, J.S.; Chung, D.M.; Maitra, K.; Maitra, S.; Stigers, K.D.; Sun, Y. *J. Am. Chem. Soc.* 2000, 122, 7654–7661.
Cornish, V. W.; Mendel, D.; Schultz, P.G. *Angew. Chem. Int. Ed. Engl.* 1995, 35, 621–633.
Voyer, N.; Lamothe, J. *Tetrahedron* 1995, 51, 9241–9284.
Lam, P. Y. S.; Duedon, S.; Averill, K. M.; Li, R.; He, M. Y.; DeShong, P.; Clark, C. G. *J. Am. Chem. Soc.* 2000, 122, 7600.
Johnston, J.N.; Plotkin, M. A.; Viswanathan, R.; Prabhakaran, E. N. *J. Am. Chem. Soc.*, submitted Sep. 20, 2000.
Gellman, S. H. *Acc. Chem. Res.* 1998, 31, 173–180.
O'Donnell, M. J.; Delgado, F.; Pottorf, R. S. *Tetrahedron* 1999, 55, 6347–6362.
O'Donnell, M. J.; Zhou, C.; Scott, W. L. *J. Am. Chem. Soc.* 1996, 118, 6070–6071.
Juaristii, E.; Quintana, D.; Escalante, J. *Aldrichimica Acta* 1994, 27, 3–10.
Cole, D. C. *Tetrahedron* 1994, 50, 9517–82.
Calmes, M.; Escale, F. *Tetrahedron: Asymmetry* 1998, 9, 2845.
Bergman, R. G. *Acc. Chem. Res.* 1973, 6, 25–31.
Smith, A. L.; Nicolaou, K. C. *J. Med. Chem.* 1996, 39, 2103–2117.
Smith, J. A.; Bifulco, G.; Case, D. A.; Boger, D. L.; Gomez–Paloma, L.; Chazin, W. J. *J. Mol.Biol.* 2000, 300, 1195–1204.
Darby, N.; Kim, C. U.; Salaun, J. A.; Shelton, K. W.; Takada, S.; Masamune, S. *J. Chem. Soc. (D)*, 1971, 23, 1516–1517.
Tanaka, H.; Yamada, H.; Matsuda, A.; Takahashi, T.* *SynLett*, 1997, 381–383.
Pickard, P. L.; Tolbert, T. L. in "Organic Syntheses"; Wiley: NY, 1973, Collective vol. 5, pp. 520–522.
O'Donnell, M. J.; Polt, R. L. *J. Org. Chem.* 1982, 47, 2663.
Halab, L.; Lubell, W. D. (1999). Use of steric interactions to control peptide turn geometry. Synthesis of Type VI β–Turn Mimics with 5–tert–butylproline. *J. Org. Chem.* 64, 3312–3321.

* cited by examiner

AMINATION PROCESS

FIELD OF THE INVENTION

The present invention belongs to the field of synthetic organic chemistry. In particular, it relates to a process for forming carbon-nitrogen bonds, particularly vinyl-nitrogen bonds and aryl-nitrogen bonds.

BACKGROUND OF THE INVENTION

The development of methods that effect the formation of carbon-nitrogen bonds is a challenge of broad interest due to the prevalence of the aniline subunit within many biologically-active natural products and medicinal agents (See, e.g., *The Alkaloids: Chemistry and Biology*, Cordell, G. A., Ed.; Academic: San Diego, 1998, Vol. 50). Significantly, indole alkaloid syntheses frequently commence from one of many available aniline or indole derivatives. Although this strategy is inherently limited, its popularity is perhaps due to the fact that there are few methods available for forming aryl-nitrogen bonds. Moreover, existing technology generally fails to offer the mild conditions necessary for the highest degree of chemoselectivity. Transition-metal mediated aryl amination generally requires the use of a basic additive to promote the coupling process. Moreover, transition metal ligand selection is based upon consideration of the individual electronic nature of the aromatic halide (or triflate, etc.) and amine components.

Similar, but fewer, methods are available for vinyl amination. Again, the need for basic and/or nucleophilic addends limits the substrate generally of these methodologies. Metal-mediated alkyne amination offers alternative access to the products of vinyl amination (enamines), but functional group tolerance is attenuated further still. Notwithstanding the technological limitations, the products of these transformations are valuable both as synthetic intermediates and as targets themselves. Of particular importance is the pyrrolidine heterocyclic class and its oxidized variants (dihydropyrrole and pyrrole). For example, 2-carboxy pyrrolidine is also known as proline, an a-amino acid prevalent in biopeptides. The pyrrolidine backbone is also found in medicinal agents (i.e., drugs) and numerous classes of natural products displaying a range of biological activity.

SUMMARY OF THE INVENTION

The present invention provides methodology for carbon-nitrogen bond formation via vinyl or aryl amination. In the process of the invention, an $sp^2$ hybridized radical is reacted with an azomethine moiety to form dihydropyrrole, 2-methylenopyrrolidine, and indoline compounds. The methodology provides a facile process for the synthesis of compounds having the pyrrolidine or indoline subunit and is especially advantageous for compounds having acid or base labile functional groups and/or is comprised of chiral centers susceptible to acidbase epimerization.

DETAILED DESCRIPTION OF THE INVENTION

In a first aspect, the present invention provides a process for forming an intramolecular carbon-nitrogen bond which comprises reacting an $sp^2$ hybridized carbon radical moiety with an azomethine moiety in the presence of a hydrogen atom donor, wherein said azomethine moiety possesses at least one radical stabilizing group, and the azomethine carbon is in the ketone oxidation state or higher. In this regard, suitable radical stabilizing groups are known in the art and include but are not limited to the following: phenyl, vinyl, trifluormethyl, carbonyl, and the like. In a preferred embodiment, the azomethine carbon will be in the ketone oxidation state and will be bonded by groups such as hydrocarbyl, substituted hydrocarbyl, aryl, and heteroaryl, provided that the atom bonded between such groups and the azomethine carbon is a carbon atom.

As used herein, the term "azomethine" preferably refers to the subunit having the Formula

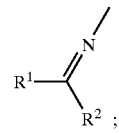

wherein $R^1$ and $R^2$ are as defined herein.

In this process, the $sp^2$ hybridized radical can be formed using any number of methodologies, including but not limited to preparation of the desired carbon radical moiety by photolysis, thermal cleavage, or by homolytic transmetalation in the presence of a free radical initiator compound. In the latter case, the substituted carbon moiety will thus preferably be substituted by a suitable radical leaving group such as a halogen atom. The term "free radical intitiator" compound is any compound which is capable of facilitation of a free radical reaction via a homolytic mechanism. Examples include azonitrile compounds such as 2,2'-azobisisobutyronitrile (AIBN); peroxides; and the like. The carbon radical may also be produced via a prior homolytic reaction, including but not limited to a radical addition to an olefin or the thermal cyclization of an ene-diyne moiety.

Preferred "hydrogen atom donor" compounds include reactants or species which can be generated in situ which provide a hydrogen atom. Examples of suitable hydrogen donor compounds include organostannane hydrides, organosilyl silanes, organogermanium hydrides, 1,4-cyclohexadiene, γ-terpinene, thiols, selenol, and the like. Examples of organostannane hydrides include compounds of the Formula $(X')_3Sn-H$, wherein X' is an alkyl group, preferably a $C_1-C_6$ alkyl group, aryl group, or a fluorous dervative thereof. Alternatively, such a compound can be generated in situ; for example, hexamethylditin can be photolyzed to provide the same tin radical as tri-n-butyl tin hydride plus a free radical initiator compound. Examples of alkylsilylsilanes include tris(trimethylsilyl)silane, triethylsilane, and the like.

The process of the invention is particularly well suited for the preparation of various pyrrolidine compounds. One such compound is proline (or its derivatives):

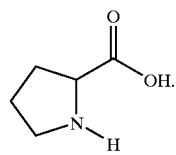

Thus, in a second aspect, the present invention provides a process for preparing a compound of Formula (2)

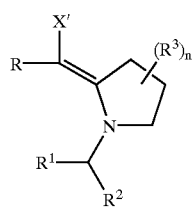

(2)

wherein each R is independently selected from the group consisting of hydrogen, hydrocarbyl, substituted hydrocarbyl, aryl, heteroaryl, substituted aryl, substituted heteroaryl, heteroatom connected hydrocarbyl, heteroatom connected substituted hydrocarbyl, heteroatom connected aryl, heteroatom connected heteroaryl, heteroatom connected substituted aryl, heteroatom connected substituted heteroaryl, a group of the formula $-C(O)R^1$, a group of the formula $-O-R^1$, a group of the formula $-NHR^1$, a group of the formula $-N(R^1)_2$, a group of the formula $-Sn(R^1)_3$, and a group of the formula $-Si(R^1)_3$;

wherein the $R^1$ and $R^2$ groups are independently selected from the group consisting of aryl, heteroaryl, hydrocarbyl, substituted aryl, substituted heteroaryl, and substituted hydrocarbyl; provided that said groups are bonded via a carbon atom;

each $R^3$ is independently selected from aryl; heteroaryl; hydrocarbyl; substituted aryl; substituted heteroaryl; substituted hydrocarbyl; heteratom connected aryl; heteroatom connected hydrocarbyl; heteroatom connected substituted hydrocarbyl; heteroatom connected heteroaryl; heteroatom connected substituted aryl; halo, preferably fluoro or chloro, most preferably fluoro; amino; cyano; hydroxy; carboxy; a group of the formula $-C(O)O-C_1-C_8$ alkyl; a group of the formula $-C(O)R^1$; a group of the formula $-O-R^1$; a group of the formula $-NHR^1$; a group of the formula $-N(R^1)_2$; $C_1-C_8$ alkoxy; $C_1-C_8$ alkylthio; and oxo (i.e., an in-line carbonyl group wherein the oxygen is doubly bonded with the carbon atom to which $R^3$ is attached, in which case n will of course be 1); or two $R^3$ groups taken together can form a divalent hydrocarbyl, substituted hydrocarbyl, or be bonded directly to a heteroatom such as oxygen, nitrogen, or sulfur; and n is from 0 to 6;

which comprises contacting a compound of Formula (1)

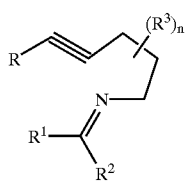

(1)

with a free radical initiator in the presence of a hydrogen atom donor, wherein R, $R^1$, $R^2$, $R^3$, and n are as defined above.

In a third aspect, there is provided a process for preparing compounds of the formula

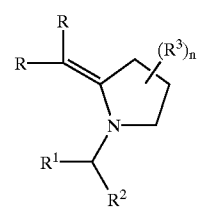

(2a)

wherein each R is independently selected from the group consisting of hydrogen, hydrocarbyl, substituted hydrocarbyl, aryl, heteroaryl, substituted aryl, substituted heteroaryl, heteroatom connected hydrocarbyl, heteroatom connected substituted hydrocarbyl, heteroatom connected aryl, heteroatom connected heteroaryl, heteroatom connected substituted aryl, heteroatom connected substituted heteroaryl, a group of the formula $-C(O)R^1$, a group of the formula $O-R^1$, a group of the formula $-NHR^1$, a group of the formula $-N(R^1)_2$, a group of the formula $-Sn(R^1)_3$, and a group of the formula $Si(R^1)_3$;

wherein the $R^1$ and $R^2$ groups are independently selected from the group consisting of aryl, heteroaryl, hydrocarbyl, substituted aryl, substituted heteroaryl, and substituted hydrocarbyl; provided that said groups are bonded via a carbon atom;

each $R^3$ is independently selected from aryl; heteroaryl; hydrocarbyl; substituted aryl; substituted heteroaryl; substituted hydrocarbyl; heteratom connected aryl; heteroatom connected hydrocarbyl; heteroatom connected substituted hydrocarbyl; heteroatom connected heteroaryl; heteroatom connected substituted aryl; amino; halo; cyano; hydroxy; carboxy; a group of the formula $-C(O)O-C_1-C_8$ alkyl; a group of the formula $-C(O)R^1$; a group of the formula $O-$; a group of the formula $-NHR^1$; a group of the formula $-N(R^1)_2$; $C_1-C_8$ alkoxy; $C_1-C_8$ alkylthio; and oxo; or two $R^3$ groups taken together can form a divalent hydrocarbyl, substituted hydrocarbyl, or be bonded directly to a heteroatom selected from oxygen, nitrogen, or sulfur; and each n is 0, 1 or 2;

which comprises contacting a compound of the formula

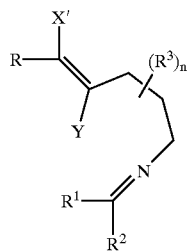

with a free radical initiator in the presence of a hydrogen atom donor, wherein Y is a radical leaving group, and X' is a group selected from $C_1-C_6$ alkyl, aryl, or a fluorous derivative thereof.

The compounds of Formula (2) and (2a) can thus be derivatized to form proline by epoxidation and acid-catalyzed rearrangement to the amino aldehyde. Oxidation and deprotection of the amnine provides proline; in this fashion, proline and other prolie-subunit containing compounds may be synthesized using intermediates of Formula (2). Thus, as a fourth aspect of the invention, there is provided the second aspect of the invention as set forth above, further comprising the steps:

(a) epoxidation, followed by acid catalyzed rearrangement to afford an amino aldehyde, of the formula

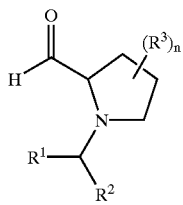

followed by (b) treatment of the resulting aldehyde with a suitable inorganic oxidizing agent, (c) followed by deprotection of the nitrogen to provide proline, wherein $R^1$, $R^2$, $R^3$, and n are as defined above.

In this regard, suitable inorganic oxidizing agents include chromic acid, and suitable methodologies for removal of the $R^1$ and $R^2$ groups (i.e., deprotection of the nitrogen) include conventional hydrogenation utilizing, for example, $H_2$, PdC, $HCO_2H$ or HCl, in diethyl ether followed by appropriate workup.

As an alternative to the alkyne starting material of Formula (1) above, one may utilize the corresponding vinyl halide of Formula (3)

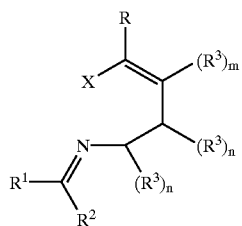

(3)

wherein R, $R^1$, $R^2$, and $R^3$, and n are as defined above, m is zero or one (in which case, the carbon to which $R^3$ is attached will be substituted by hydrogen), and X is a halide such as bromo, iodo, or chloro, which provides access to dihydropyrrolidine ring systems having the formula

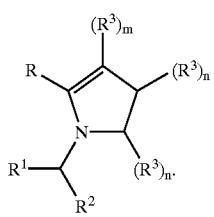

(4)

In the above formula (3), it will be understood that the $(R^3)n$ group represents that there may be one, two or no such $R^3$ groups at the 4 and 5 positions of the dihydropyrrole ring. It will also be understood that either olefin stereoisomer may be utilized in the above method insofar as the vinyl radical stereoisomers epimerize rapidly and only one leads to the cyclized product.

Thus, in a fifth aspect, the present invention provides a process for preparing a compound of the Formula (4)

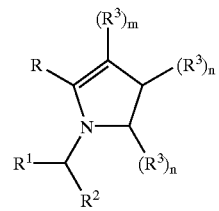

(4)

wherein each R is independently selected from the group consisting of hydrogen, hydrocarbyl, substituted hydrocarbyl, aryl, heteroaryl, substituted aryl, substituted heteroaryl, heteroatom connected hydrocarbyl, heteroatom connected substituted hydrocarbyl, heteroatom connected aryl, heteroatom connected heteroaryl, heteroatom connected substituted aryl, heteroatom connected substituted heteroaryl, a group of the formula —$C(O)R^1$, a group of the formula —O—$R^1$ a group of the formula —$NHR^1$, a group of the formula —$N(R^1)_2$, a group of the formula —$Sn(R^1)_3$, and a group of the formula —$Si(R^1)_3$;

wherein the $R^1$ and $R^2$ groups are independently selected from the group consisting of aryl, heteroaryl, hydrocarbyl, substituted aryl, substituted heteroaryl, and substituted hydrocarbyl; provided that said groups are bonded via a carbon atom;

each $R^3$ is independently selected from aryl; heteroaryl; hydrocarbyl; substituted aryl; substituted heteroaryl; substituted hydrocarbyl; heteratom connected aryl; heteroatom connected hydrocarbyl; heteroatom connected substituted hydrocarbyl; heteroatom connected heteroaryl; heteroatom connected substituted aryl; amino; halo; cyano; hydroxy; carboxy; a group of the formula —$C(O)O$—$C_1$–$C_8$ alkyl; a group of the formula —$C(O)R^1$; a group of the formula —O—$R^1$; a group of the formula —$NHR^1$; a group of the formula —$N(R^1)_2$; $C_1$–$C_8$ alkoxy; $C_1$–$C_8$ alkylthio; and oxo; or two $R^3$ groups taken together can form a divalent hydrocarbyl, substituted hydrocarbyl, or be bonded directly to a heteroatom selected from oxygen, nitrogen, or sulfur; m is 0 or 1; and each n is 0, 1 or 2;

which comprises contacting a compound of the Formula (3)

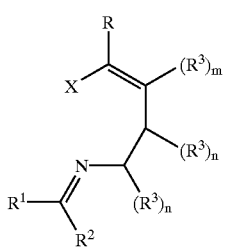

(3)

wherein R, $R^1$, $R^2$, and $R^3$, and n are as defined for Formula (4), and X is a halide, with a free radical initiator in the presence of a hydrogen atom donor.

In the process of this aspect of the invention, the desired radical may be generated in situ using methodology described above with regard to the first aspect. Thus, in a further embodiment, there is provided the free radical intermediate of the Formula

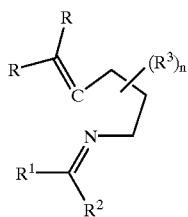

wherein R, $R^1$, $R^2$, $R^3$ and n are as defined above, which is useful as an intermediate in the preparation of the compounds of Formula (2).

The advantages of the methodology of this invention include the readily-available amino-alkyne substrates of Formula (1) as depicted above, as well as the use of radical intermediates and reaction conditions which are pH neutral. Thus, no acid or base addends are necessary to effect the desired transformation. This feature is especially advantageous when the desired pyrrolidine compound possesses acid or base labile functional groups and/or is comprised of chiral center(s) susceptible to acidbase-catalyzed epimerization. Moreover, there are no electronic restrictions on the substrates, and thus acid- and base-sensitive substrates that are electron rich, electron neutral, or electron deficient may be utilized. This addition of vinyl radicals to the nitrogen of an azomethine moiety may result in excess of 10:1, preferably 20:1 regioselectivity for the desired carbon-nitrogen bond formation. In contrast to other methodologies for amination, the active nitrogen-containing component in each case is an azomethine, and the pi-bond is its reactive feature (as opposed to a sigma N—H bond).

In the above Formulae (1) and (2), it will be understood that the indeterminate placement of the $R^3$ group(s) denotes that there may be none or up to 6 of such groups at the carbon atoms α, β, and γ to the nitrogen atom. In this regard, the possible substituents from which $R^3$, as well as $R^1$ and $R^2$ may be selected is not particularly limited, so long as such groups do not contain species which have a deleterious effect on the desired reaction or otherwise serve to quench the $sp^2$-hybridized carbon radical prematurely.

Further examples of starting materials (1) of the present invention include (Z) or (E)-vinyl halides. In addition, the process of the present invention may be conducted on substrates which are attached to a solid support via any carbon of the required structural features. In addition, the process of the present invention may be utilized in the construction of combinatorial libraries of compounds. Utilizing the methodology of the present invention, entantiomerically enriched starting materials may be utilized to prepare enantimerically enriched final products.

The methodology of the present invention is also useful in the context of aryl amination. Thus, in a third aspect, the present invention provides a process for forming a carbon-nitrogen bond, wherein said carbon is part of an aryl or heteroaryl ring, which comprises reacting an aryl or heteroaryl radical moiety with an azomethine moiety in the presence of a hydrogen atom donor in an intramolecular reaction to form a fused ring system, wherein said azomethine moiety possesses at least one radical stabilizing group, and the azomethine carbon is in the ketone oxidation state or higher.

As noted above, the process of the present invention is particularly well suited for the synthesis of a wide variety of substituted indoline species. In this regard, the phenyl ring in the indoline ring system may possess one or more heteroatoms and may be fused to one or more aryl or heteroaryl rings, so long as there is an $sp^2$ hybridizable carbon atom alpha to the point of attachment of the tethered azomethine.

Thus, in a sixth aspect, there is provided a process for preparing compounds of the formula ($R^8$)$_n$-(fused aryl and/or heterocyclic ring)

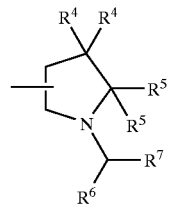

wherein each of the groups $R^4$, $R^5$, and $R^8$ are independently selected from hydrogen, aryl; heteroaryl; hydrocarbyl; substituted aryl; substituted heteroaryl; substituted hydrocarbyl; heteratom connected aryl; heteroatom connected hydrocarbyl; heteroatom connected substituted hydrocarbyl; heteroatom connected heteroaryl; heteroatom connected substituted aryl; halo; amino; cyano; hydroxy; carboxy; a group of the formula —C(O)O—$C_1$–$C_8$ alkyl; a group of the formula —C(O)$R^1$; a group of the formula —O—$R^1$; a group of the formula —NH$R^1$; a group of the formula —N($R^1$)$_2$; $C_1$–$C_8$ alkoxy; $C_1$–$C_8$ alkylthio; or two of $R^5$ and $R^6$, and/or two $R^8$ groups taken together can form a divalent hydrocarbyl, substituted hydrocarbyl, or be bonded directly to a heteroatom selected from oxygen, nitrogen, or sulfur; and n is from 0 to however many available sites exist on the ring system, for example, 4 in the case of phenyl and 6 in the case of napthyl;

in addition, two $R^4$ groups and/or two $R^5$ groups can be taken together represent oxo;

$R^6$ and $R^7$ are independently selected from aryl, heteroaryl, hydrocarbyl, substituted aryl, substituted heteroaryl, and substituted hydrocarbyl; provided that said groups are bonded via a carbon atom;

and n is from 0 to 4;

which comprises contacting a compound of the formula ($R^8$)$_n$-(fused aryl and/or heterocylclic ring)

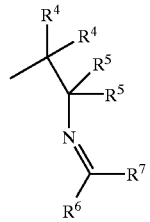

wherein said fused aryl and/or heterocyclic ring possesses a carbon alpha to its point of attachment capable of forming an $sp^2$ hybridized carbon radical, said carbon substituted by a group Y, wherein Y is a radical leaving group;

with a free radical initiator in the presence of a hydrogen atom donor.

In this aspect of the invention, it should be appreciated that the groups which are suitable in this process as "fused aryl and/or heterocyclic rings" include aryl and heteroaryl groups as set forth below, optionally substituted by one or more $R^8$ groups. By way of example, if the fused aryl and/or heterocyclic ring is pyridine, one possible ring structure which can be obtained via this process has the formula:

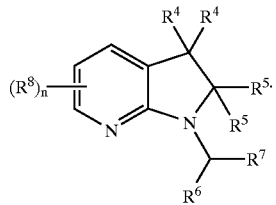

Similarly, if the "fused aryl and/or heterocyclic ring" is benzothiophene, one possible ring system which can be obtained via this process has the formula:

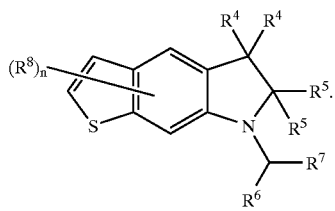

As noted above, the process of the present invention is especially useful in the preparation of indoline ring systems. Thus, in a fifth aspect, the present invention provides a process for preparing a compound of Formula (4)

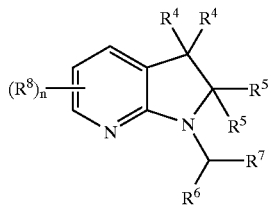

wherein each of the groups $R^4$, $R^5$, and $R^8$ are independently selected from hydrogen, aryl; heteroaryl; hydrocarbyl; substituted aryl; substituted heteroaryl; substituted hydrocarbyl; heteratom connected aryl; heteroatom connected hydrocarbyl; heteroatom connected substituted hydrocarbyl; heteroatom connected heteroaryl; heteroatom connected substituted aryl; halo; amino; cyano; hydroxy; carboxy; a group of the formula —C(O)O—$C_1$–$C_8$ alkyl; a group of the formula —C(O)$R^1$; a group of the formula —O—$R^1$; a group of the formula —NHR'; a group of the formula —N($R^1$)$_2$; $C_1$–$C_8$ alkoxy; $C_1$–$C_8$ alkylthio; or two of $R^5$ and $R^6$, or two $R^8$ groups taken together can form a divalent hydrocarbyl, substituted hydrocarbyl, or be bonded directly to a heteroatom selected from oxygen, nitrogen, or sulfur;

in addition, two $R^4$ groups and/or two $R^5$ groups can be taken together represent oxo;

$R^6$ and $R^7$ are independently selected from aryl, heteroaryl, hydrocarbyl, substituted aryl, substituted heteroaryl, and substituted hydrocarbyl; provided that said groups are bonded via a carbon atom;

and n is from 0 to 4;
which comprises contacting a compound of Formula (3)

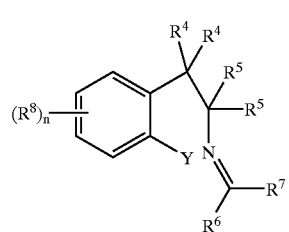

with a free radical initiator in the presence of a hydrogen atom donor, wherein Y is a radical leaving group.

In the process of this aspect of the invention, the desired radical may be generated in situ using methodology described above with regard to the first aspect. Thus, in a further embodiment, there is provided the free radical intermediate of the Formula (5)

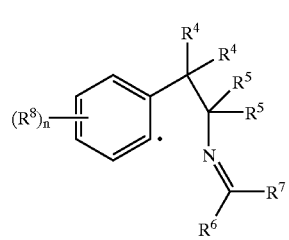

which is useful as an intermediate in the preparation of the compounds of Formula (4).

In a further preferred embodiment of this aspect, the invention is useful in the preparation of chiral products, iLe., intermediates and products in which the product of the process is enantiomerically enriched. In this regard, in the case where one of the $R^5$ groups is carboxy, such a chiral synthetic route allows for the preparation of indoline α-amino acids.

The advantages of the methodology of this invention include the readily-available aryl radical precursors (e.g., aryl halides), readily available phenethyl amine derivatives and carbonyl compounds, as well as the use of radical intermediates and reaction conditions which are pH neutral. Thus, no acid or base addends are necessary to effect the desired transformation. This feature is especially advantageous when the desired indole compound possesses acid or base labile functional groups and/or is comprised of chiral center(s) susceptible to acidbase-catalyzed epimerization. Moreover, there are no electronic restrictions on the substrates (3), and thus acid- and base-sensitive substrates that are electron rich, electron neutral, or electron deficient may be utilized. This addition of aryl radicals to the nitrogen of an azomethine moiety may result in excess of 10:1, more often 20:1 regioselectivity for the desired nitrogen-carbon bond formation. In contrast to other methodologies for amination, the active nitrogen-containing component in each case is an azomethine, and the pi-bond is its reactive feature (as opposed to a sigma N—H bond).

In the above Formulae (3), (4), and (5), it will be understood that the indeterminate placement of the $R^8$ groups denotes that there may be none or up to 4 such groups at the carbon atoms of the phenyl ring. Thus, the process of this aspect of the invention should be recognized as a general methodology for the synthesis of indole and subsituted indole species. In this regard, the possible substituents from which $R^8$, as well as $R^4$, $R^5$, $R^6$, and $R^7$ may be selected is not particularly limited, so long as such groups do not contain species which have a deleterious effect on the desired reaction or otherwise serve to quench the sp²-hybridized carbon radical prematurely. Insofar as such groups are not limited by acidbase sensitivity or by electonic features, the above process is useful for making a broad range of compounds containing the indole subunit. By way of illustration of the robust nature of the process of the present invention, one $R^4$ group and one $R^5$ group could be taken together to form an aziridine ring system.

Examples of particularly preferred substrates of Formula (3) include homochiral indoline α-amino acids, substituted indolines, etc.

It is this flexibility which renders the above methodologies especially suited for the construction of libraries of compounds, insofar as wide varieties of electron-rich as well as electron-deficient amine and ketone starting materials can be utilized to prepare the azomethine species and in all such cases, provided the above parameters are met, will result in the formation of intramolecular carbon-nitrogen bond formation. Thus, in a further aspect, there is provided a process for the synthesis of a library of compounds having a proline, indoline, or indole subunit, which comprises application of the methodology herein.

In each of the above aspects of the process of the present invention, the process may be conducted neat or in a nonparticipating solvent such as benzene.

Also, in each of the above aspects of the invention, the methods may be conducted with the substrate attached to a solid support.

Other desired reaction conditions for the process of the present invention are not particularly critical and may in any event be chosen and optimized by one of ordinary skill in the art.

In this disclosure certain chemical groups or compounds are described by certain terms and symbols. These terms are defined as follows:

Symbols ordinarily used to denote elements in the Periodic Table take their ordinary meaning, unless otherwise specified. Thus, N, O, S, P, and Si stand for nitrogen, oxygen, sulfur, phosphorus, and silicon, respectively.

A "hydrocarbyl" group means a monovalent or divalent, linear, branched or cyclic group which contains only carbon and hydrogen atoms. Examples of monovalent hydrocarbyls include the following: $C_1$–$C_{20}$ alkyl; $C_1$–$C_{20}$ alkyl substituted with one or more groups selected from $C_1$–$C_{20}$ alkyl, $C_3$–$C_8$ cycloalkyl, or aryl; $C_3$–$C_8$ cycloalkyl substituted with one or more groups selected from $C_1$–$C_{20}$ alkyl, $C_3$–$C_8$ cycloalkyl, or aryl.

A "substituted hydrocarbyl" refers to a monovalent or divalent hydrocarbyl substituted with one or more heteroatoms. Examples of monovalent substituted hydrocarbyls include: —C(O)$R^{13}$ (wherein $R^{13}$ is hydrocarbyl), —C(O)NR$^{13}_2$ (wherein $R^{13}$ is hydrocarbyl), 2-hydroxyphenyl, 2-methoxyphenyl, 2-ethoxyphenyl, 2-fluorophenyl, 2-chlorophenyl, 2-trifluoromethylphenyl, 2,6-bis(trifluoromethyl)phenyl, 2-(trialkylsiloxy)phenyl, 2-(triarylsiloxy)phenyl, 2,6-bis(diphenylamino)phenyl, 2,6-bis(phenoxy)phenyl, 2-hydroxy-6-phenylphenyl, 2-cyanophenyl, 2-(diphenylamino)phenyl, 4-nitrophenyl, 2-nitrophenyl, —CH$_2$OR$^{13}$ (wherein $R^{13}$ is hydrocarbyl), cyano, —CH$_2$NR$^{13}_2$ (wherein $R^{13}$ is hydrocarbyl), and —CH$_2$OSiR$^{13}_3$ (wherein $R^{13}$ is hydrocarbyl). Also encompassed by the term "substituted hydrocarbyl" are hydrocarbyl groups having one or more groups selected from arnide, imido, carbonyl, carboxy, hydroxy, cyano, nitro, halo, alkoxy, alkoxycarbonyl, carboxamido groups, as well as unsubstituted and substituted carboxylic acid ester, unsubstituted and substituted carbamoyl, and substituted imino, as such terms are defined herein. Moreover, such substituted hydrocarbyl groups can form aliphatic ring systems containing one or more heteroatoms and various alkylene linkages such as methylene, ethylene, propylene, etc. Examples of such ring systems include but are not limited to tetrahydrofuran, pyrrolidine, tetrahydropyran, piperidine, and the like.

Examples of the term "aryl" include a unsubstituted $C_6$–$C_{14}$ aryl group as well as a $C_6$–$C_{14}$ aryl substituted with one or more groups selected from $C_1$–$C_{20}$ alkyl, $C_3$–$C_8$ cycloalkyl, aryl, amide, imido, carbonyl, carboxy, hydroxy, cyano, nitro, halo, alkoxy, alkoxycarbonyl, carboxamido groups, as well as unsubstituted and substituted carboxylic acid ester, unsubstituted and substituted carbamoyl, and substituted imino, as such terms are defined herein, and wherein the term "aryl" preferably denotes a phenyl, napthyl, or anthracenyl group.

A "heteroatom" refers to an atom other than carbon or hydrogen. Preferred heteroatoms include oxygen, nitrogen, phosphorus, sulfur, selenium, arsenic, chlorine, bromine, silicon and fluorine. In this regard, the terms "heteratom connected aryl", "heteroatom connected hydrocarbyl" and like terms indicate that a heteroatom is the point of attachment for such a group. An example of a heteroatom connected hydrocarbyl would thus be butanethiol, an example of a heteroatom connected aryl would be phenoxy, and an example of a heteroatom connected heteroaryl would be 1-pyrrolyl.

The term "heteroaryl" as used herein preferably refers to heterocyclic aryl rings having one or more heteroatoms. Preferably, such heteroaryl groups are stable 5- to 7-membered monocyclic or bicyclic or 7- to 10-membered bicyclic heterocyclic rings which are saturated partially unsaturated or unsaturated (aromatic), and which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. Examples of heterocyclic rings include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, .beta.-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, lH-indazolyl, indolenyl, indolinyl, indolizinyl, indolyl, isobenzofuranyl, isochromanyl, isoindazolyl, isoindolinyl, isoindolyl, isoquinolinyl isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl., oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred heterocycles include, but are not limited to, pyridinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinoyl.

The terms "substituted aryl" and "substituted heteroaryl" refers to such aryl and heterocyclic rings substituted by one or more halogen, $C_1$–$C_6$ alkyl, phenoxy, phenyl, hydroxy, amino, $C_1$–$C_6$ alkoxycarbonyl, nitro, $C_1$–$C_6$ alkylsulfonyl, carboxy, cyclohexyl, carbamoyl, cyano, $C_1$–$C_6$ alkylsulfonylamino or $C_1$–$C_6$ alkoxy groups, amido, imido, cyano, nitro, $C_1$–$C_6$ alkoxy, $C_1$–$C_6$ carboxamido groups, as well as unsubstituted and substituted carboxylic acid ester, unsubstituted and substituted carbamoyl, and substituted imino, as such terms are defined herein.

The term "alkoxycarbonyl" refers to an alkoxy group bonded to a carbonyl function. In other words, the $C_2$ alkoxycarbonyl group is ethoxycarbonyl. The term "substituted alkoxycarbonyl" refers to a $C_1$–$C_6$ alkoxycarbonyl group substituted with one or more halogen, phenyl, phenoxy, hydroxy, amino, $C_1$–$C_6$ alkoxycarbonyl, carboxy, cyclohexyl, carbamoyl, cyano, $C_1$–$C_6$ alkylsulfonylamino, or $C_1$–$C_6$ alkoxy groups.

The terms "alkyl" and "alkylene" as used herein preferably refer to $C_1$–$C_{12}$ straight or branched chain alkyl and alkylene groups, respectively. The terms "lower alkenyl" and "lower alkynyl" refer to $C_3$–$C_6$ alkenyl groups and $C_3$–$C_6$ alkynyl groups, respectively.

The term "unsubstituted and substituted carboxylic acid ester" refers to a $C_1$–$C_8$ alkyl, $C_3$–$C_8$ cycloalkyl or aryl oxycarbonyl group, preferably containing from 2 to 10 carbon atoms and optionally substituted with halogen, $C_1$–$C_6$ alkoxy, $C_3$–$C_8$ cycloalkyl, aryl, aryloxy, $C_1$–$C_6$ alkyl, cyano, $C_1$–$C_6$ alkanoyloxy, hydroxy or $C_1$–$C_6$ alkoxycarbonyl.

The term "unsubstituted and substituted carbamoyl" refers to an alkyl (or substituted alkyl) amino carbonyl group, preferably containing from 2 to 10 carbon atoms.

The term "substituted imino" refers to an imino group substituted with a group selected from hydrogen, $C_1$–$C_6$ alkyl, $C_3$–$C_8$ cycloalkyl or aryl.

The term "radical leaving group" will be understood by those skilled in the art to denote groups such as iodo, bromo, diazonium salts, and the like.

The term "solid support" as used herein preferably refers to solid supports known in the art of synthetic chemistry as inert materials which are attached to a substrate, upon which one or more synthetic manipulations is to be carried out. This material upon which the processes of the invention are performed are referred to as solid supports, beads and resins.

These terms are intended to include: beads, pellets, disks, fibers, gels or particles such as cellulose beads, pore-glass beads, silica gels, polystyrene beads optionally cross-linked with divinylbenzene and optionally grafted with polyethylene glycol and optionally functionalized with amino, hydroxy, carboxy or halo groups, grafted co-poly beads, polyacrylamide beads, latex beads, dimethylacrylamide beads optionally cross-linked with N,N'-bis-acryloyl ethylene diamine, glass particles coated with hydrophobic polymer, etc., i. e., material having a rigid or semi-rigid surface and soluble supports such as low molecular weight non-cross-linked polystyrene.

The following examples are set forth merely as illustrations of the invention and are not intended to be considered limiting as to the scope thereof.

Experimental Section

Flame-dried (under vacuum) glassware was used for all non-aqueous reactions. All reagents and solvents were commercial grade and purified prior to use when necessary. Diethyl ether ($Et_2O$), tetrahydrofuran (THF), dichloromethane ($CH_2Cl_2$), and benzene ($C_6H_6$) were dried by passage through a column of activated alumina as described by Grubbs (See Pangbom, A. B.; Giardello, M. A.; Grubbs, R. H.; Rosen, R. K.; Timmers, F. J. *Organometallics* 1996, 15, 1518–1520.) Benzene was additionally passed through a column containing activated Q-5 reactant. Solvents other than benzene were degassed using the freeze-pump-thaw method when necessary. All additional solvents were dried by distillation from calcium hydride when necessary. Molecular sieves (spheres, 4 Å) were calcined at 400° C. and stored at room temperature in an air-tight container. AIBN was recrystallized prior to use, and tri-n-butyl tin hydride ("$Bu_3SnH$") was used as received from Aldrich. Preparations for previously unreported phenethyl amine derivatives used in this study will be reported later in an Article after optimization.

Thin layer chromatography (TLC) was performed using glass-backed silica gel (250 $\mu$) plates and flash chromatography utilized 230–400 mesh silica gel from Scientific Adsorbents. Neutral Alumina was used as received from Scientific Adsorbents for chromatography of acid-sensitive intermediates or products. Products were visualized by UV light, iodine, and/or the use of ceric ammonium molybdate, potassium permanganate, ninhydrin, p-anisaldehyde, and potassium iodoplatinate solutions.

IR spectra were recorded on a Nicolet Avatar 360 spectrophotometer. Liquids and oils were analyzed as neat films on a salt plate (transmission), whereas solids were applied to a diamond plate (ATR). Nuclear magnetic resonance spectra (NMR) were acquired on either a Varian Inova-400 or VXR-400 instrument. Chemical shifts are measured relative to tetramethylsilane, as judged by the residual partially deuterated solvent peak. Mass spectra were obtained using a Kratos MS-80 spectrometer using the ionization technique indicated. Combustion analyses were performed on a Perkin-Elmer 2400 Series II CHNSO Analyzer.

Ratios of diastereomers and isomeric products were measured directly from integration of $^1H$ NMR absorptions of protons common to the components. Precision was checked by varying the relaxation delay for measurements on the same compound. Where possible, ratios were corroborated using GC-mass spectrometry. Peak assignments were made from authentic samples in every case. Ratios reported generally represent a lower limit defined by multiple runs.

General Procedure for Ketimine Condensations

A rapidly stirred benzene solution of the amine (0.5 M), ketone (0.5 M), and 4 Å MS (1:1 ww) was stirred at 25° C. until complete conversion was achieved, as evidenced by $^1$H NMR. The mixture was filtered through a pad of Celite and washed with Et2O or benzene. The solvent was removed in vacuo to give the analytically pure ketimine which was used immediately.

The same procedure was used when the benzophenone ketimine was desired, except benzophenone imine (Pickard, P. L.; Tolbert, T. L., in "Organic Syntheses"; Wiley: NY, 1973, Collective Vol. 5, pp. 520–2) was used in place of the ketone. (O'Donnell, M. J.; Polt, R. L. *J. Org. Chem.* 1982, 47, 2663.)

General Procedure for Aryl Aminations

A benzene solution of the ketimine (0.01 M) was warmed to 85° C. in a round-bottomed flask equipped with a condenser. A benzene solution (1 mL) of nBu3SnH (1.1 equiv) and AIBN (0.4 equiv) was loaded into a gas-tight syringe and was attached to a syringe pump. The syringe needle was attached through a septum at the top of the condenser (wN$_2$ line) so that the solution droplets would fall directly into the refluxing benzene. Following the addition, the reaction mixture was refluxed for an additional period (~1 h) and cooled to room temperature. At this point, an aliquot was removed, concentrated, and component ratios were measured by $^1$H NMR and/or GC-MS. The solution was treated with NaBH$_4$ (1.1 equiv) and the slurry was stirred 4–5 hours. The mixture was concentrated in vacuo, diluted with Et$_2$O, and washed with water. The organic layer was separated, dried (MgSO$_4$), and concentrated to furnish an oil. Flash chromatography of the crude mixture provided the analytically pure targeted compounds.

EXAMPLE 1

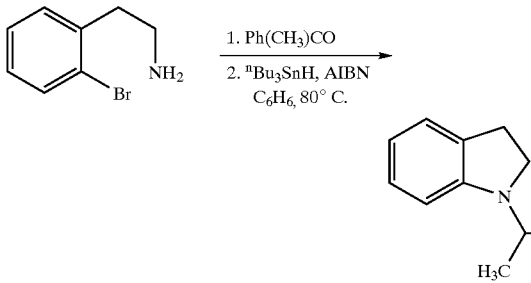

N-(1-Methylbenzyl)indoline (2a).

Following the general procedure, o-bromophenethylamine (46 mg, 231 mmol), acetophenone (27 μL, 231 mmol), and 4 Å MS were stirred in benzene (1 mL) at room temperature for 12 h. Filtering of the mixture through Celite and removal of the solvent provided the ketimine as a >95:5 mixture of stereoisomers. IR (film) 3056, 1633 cm$^{-1}$; $^1$H NMR (400 MHz, CDCl$_3$) δ7.78 (m, 2H), 7.57 (d, J=6.9 Hz, 2H), 7.40 (t, J=3.1 Hz, 3H), 7.34 (d, J=6.0 Hz, 1H), 7.26 (t, J=6.3 Hz, 1H), 7.10 (t, J=6.0 Hz, 1H), 3.79 (dd, J=7.8, 7.8 Hz, 2H), 3.22 (dd, J=7.8, 7.8 Hz, 2H), 2.17 (s, 3H); $^{13}$C NMR (100 MHz, CDCl$_3$) ppm 166.0, 142.0, 140.0, 133.0, 131.7, 129.7, 128.5, 128.1, 127.6, 126.9, 52.2, 37.8, 18.1; HRMS (EI): Exact mass calcd for C$_{16}$H$_{16}$BrN [M+H]$^+$, 302.0544. Found 302.0516.

A three hour addition of a $^n$Bu$_3$SnH (68 μL, 0.25 mmol) and AIBN (15 mg, 93 μmol) solution in benzene (0.7 mL) to a refluxing solution of the unpurified ketimine (69.6 mg, 231 μmol) in benzene (23 mL) delivered, after flash chromatography (2% CH$_2$Cl$_2$ in hexanes), 44.9 mg (87%) of the desired indoline as a colorless oil. Rf=0.62 (30% CH$_2$Cl$_2$ hexanes); IR (film) 3046, 1606 cm$^{-1}$; $^1$H NMR (400 MHz, CDCl$_3$) δ 7.41 (d, J=7.5 Hz, 2H), 7.29 (t, J=7.2 Hz, 2H), 7.26 (t, J=7.2 Hz, 1H), 7.08 (d, J=7.2 Hz, 1H), 7.00 (t, J=7.8 Hz, 1H), 6.6 (t, J=7.2 Hz, 1H), 6.36 (d, J=7.8 Hz, 1H), 4.68 (q, J=6.8 Hz, 1H), 3.42 (ddd, J=18.1, 9.1, 0 Hz, 1H), 3.35 (ddd, J=15.7,7.4, 0 Hz, 1H), 2.96 (dd, J=8.5, 8.3 Hz, 2H), 2.58 (d, J=6.8 Hz, 3H); $^{13}$C NMR (100 MHz, CDCl$_3$) ppm 151.1 143.0 128.7, 127.4, 127.3, 127.1, 124.6, 117.2, 107.5, 54.8, 48.2, 28.5, 16.8; HRMS (EI): Exact mass calcd for C$_{16}$H$_{17}$N [M]$^+$, 223.1361. Found 223.1366.

EXAMPLE 2

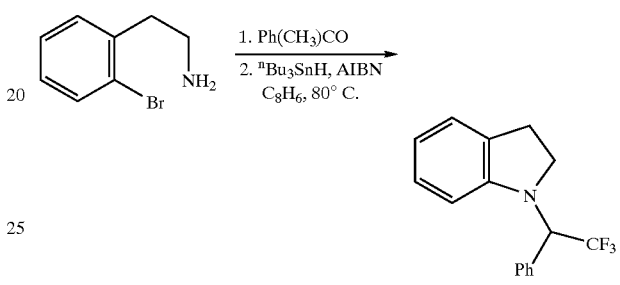

N-(1-Trifluoromethyl)benzyl indoline (2b).

Following the general procedure, o-bromophenethylamine (852 mg, 4.25 mmol), trifluoroacetophenone (590 pL, 4.21 mmol), and 4 Å MS were stirred in toluene (10 μL) at room temperature for 12 h to provide the ketimine as a >95:5 mixture of stereoisomers. IR (film) 3062, 1669 cm$^{-1}$; $^1$H NMR (400 MHz, CDCl$_3$) δ 7.49 (d, J=7.9 Hz, 1H), 7.44 (t J=7.4 Hz, 1H), 7.38 (t, J=7.1 Hz, 2H), 7.24 (t, J=7.4 Hz, 1H), 7.18 (d, J=6.0 Hz, 1H), 7.10 (t, J=6.0 Hz, 1H), 6.94 (d, J 7.1 Hz, 2H), 3.69 (dd, J=7.1, 7.1 Hz, 2H), 3.13 (dd, J=7.1, 7.1 Hz, 2H); $^{13}$C NMR (100 MHz, CDCl$_3$) ppm 138.4, 133.0, 131.7, 130.3, 130.1, 128.8, 128.4, 127.7, 127.5, 124.9, 52.8 36.8; HRMS (EI): Exact mass calcd for C$_{16}$H$_{13}$F$_3$N [M—Br]$^+$, 276.1000. Found 276.1003.

A three hour addition of $^n$Bu$_3$SnH (184 μL, 682 μmol) and AIBN (41 mg, 248 μmol) solution in benzene (2.5 mL) to a refluxing solution of the unpurified ketimine (220 mg, 620 μmol) in benzene (62 mL) delivered, after flash chromatography (5% CH$_2$Cl$_2$ in hexanes), 133 mg (77%) of the desired indoline as a colorless oil. Rf=0.35 (5% EtOAchexanes); IR (film) 3031, 1607 cm$^{-1}$; $^1$H NMR (400 MHz, CDCl$_3$) δ 7.40 (m, 5H), 7.11 (t, J=7.9 Hz, 1H), 7.09 (d, J=7.4 Hz, 1H), 6.71 (t, J=7.4 Hz, 1H), 6.62 (d, J=7.9 Hz, 1H), 5.24 (q, J=8.7 Hz, 1H), 3.62 (dd, J=14.2, 8.7, Hz, 1H), 3.19 (dd, J=10.1, 8.9, Hz, 1H), 3.01 (m, 2H); $^{13}$C NMR (100 MHz, CDCl$_3$) ppm 150.5, 131.9, 129.3, 129.0, 127.6, 127.5, 125.1, 124.7, 118.5, 106.4, 62.0 (q, J=30.5 Hz, 1C), 48.6, 28.5; HRMS (EI): Exact mass calcd for C$_{16}$H$_{14}$F$_3$N[M]$^+$, 277.1078. Found 277.1071.

EXAMPLE 3

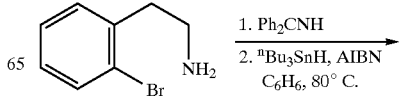

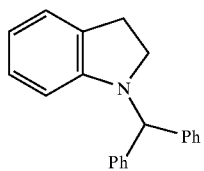

N-(1-Phenylbenzyl)indoline (2c).

Following the general procedure, o-bromophenethylamine (471 mg, 2.35 mmol) and benzophenone imine (426 mg, 2.35 mmol) were stirred for 12 h in dichloromethane (4 mL). Removal of the solvent provided the ketimine. IR (film) 3056, 1660, 1623 cm$^{-1}$; $^1$HNMR (400 MHz, CDCl$_3$) δ7.61 (d, J=6.8Hz, 2H), 7.49 (d, J=7.0 Hz, 1H), 7.40 (m, J=3.8 Hz, 3H), 7.35 (m, J=7.0 Hz, 3H), 7.24 (t, J=5.8 Hz, 1H), 7.19 (d, 6.8 Hz, 1H), 7.05 (t, J=5.8 Hz, 1H), 6.98 (m, J=3.8 Hz, 2H), 3.68 (dd, J=7.2, 7.2 Hz, 2H), 3.14 (dd, J=7.4, 7.4, Hz, 2H); $^{13}$C NMR (100 MHz, CDCl$_3$) ppm 169.0, 140.0, 139.8, 136.9, 132.9, 131.6, 130.1, 128.65, 128.61, 128.4, 128.2, 127.9, 127.4, 125.0, 53.6, 37.9; HRMS (CI): Exact mass calcd for C$_{21}$H$_{18}$BrN [M+H]$^+$, 364.0701. Found 364.0596.

A three hour addition of a $^n$Bu$_3$SnH (70 μL, 254 μmol) and AIBN (5 mg, 9.2 μmol) solution in benzene (1.0 mL) to a refluxing solution of the unpurified ketimine in benzene (23 mL) delivered, after flash chromatography (2% CH$_2$Cl$_2$ in hexanes), 56.8 mg (86%) of the desired indoline as a white solid mp 62–63° C. Rf=0.53 (10% EtOAc in hexanes); IR (film) 3025, 1605 cm$^{-1}$; $^1$H NMR (400 MHz, CDCl$_3$) δ 7.35 (m, 10H), 7.09 (d, J=7.0 Hz, 1H), 6.92 (t, J=7.5 Hz, 1H), 6.64 (t, J=7.0 Hz, 1H), 6.20 (d, J=7.5 Hz, 1H), 5.55 (s, 1H), 3.20 (dd, J=8.3, 8.2 Hz, 2H), 2.96 (dd, J=8.3, 8.2 Hz, 2H), $^{13}$C NMR (100 MHz, CDCl$_3$) ppm 152.1, 141.5, 130.5, 128.7, 128.6, 127.4, 127.3, 124.5, 117.7, 66.8, 51.6, 28.5; HRMS (EI): Exact mass calcd for C$_{21}$H$_{19}$N [M]$^+$, 285.1517. Found 285.1520.

EXAMPLE 4

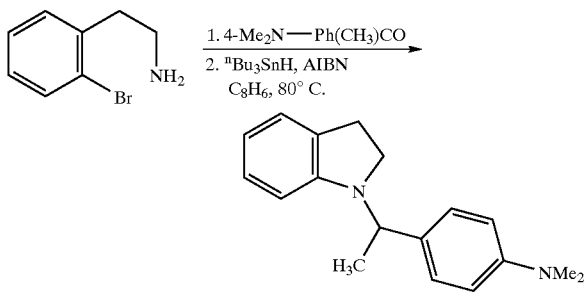

N-[(1-Methyl)-4-dimethylaminobenzyl]-indoline (2d).

According to the general procedure, o-bromophenethylamine (100 mg, 500 μmol), aceto(p-N,N'-dimethylamino)phenone (81.5 mg, 500 μmol), and 4 Å MS were stirred in benzene (6 mL) at room temperature for 4 h to provide the ketimine as a >95:5 mixture of stereoisomers. IR (film) 3050, 1602 cm$^{-1}$; $^1$H NMR (400 MHz, CDCl$_3$) δ 7.63 (d, J=9.0 Hz, 2H), 7.46 (dd, J=8.1, 1.1 Hz, 1H), 7.25 (dd, J=7.6, 1.5 Hz, 1H), 7.15 (dt, J=7.4, 1.1 Hz, 1H), 6.98 (dt, J=6.7, 1.6 Hz, 1H), 6.61 (d, J=9.0 Hz, 2H), 3.65 (t, J=7.4 Hz, 2H), 3.10 (t, J=7.4 Hz, 2H), 2.91 (s, 6H), 2.03 (s, 3H); $^{13}$C NMR (100 MHz, CDCl$_3$) ppm 165.4, 151.6, 143.1, 140.3, 132.9, 131.6, 129.5, 128.0, 124.9, 111.7, 51.9, 40.6, 38.01, 15.09; HRMS (EI): Exact mass calcd for C$_{18}$H$_{21}$BrN$_2$ [M]$^+$, 334.0888. Found 344.0824.

A five hour addition of a $^n$Bu$_3$SnH (56 μL, 207 μmol) and AIBN (12 mg, 75 μmol) solution in benzene (1 mL) to a refluxing solution of the unpurified ketimine (65 mg, 188 μmol) in benzene (18 mL) delivered, after flash chromatography (50% CH$_2$Cl$_2$ in hexanes), 45 mg (90%) of the desired indoline as a crystalline solid, mp 79–82° C.; Rf=0.15 (50% CH$_2$Cl$_2$ hexanes; IR (film) 2960, 1653 cm$^{-1}$; $^1$H NMR (400 MHz, CDCl$_3$) δ 7.28 (t, J=4.2 Hz, 2H), 7.03 (dd, J=17.5, 7.2 Hz, 2H), 6.73 (d, J=8.8 Hz, 2H), 6.50 (t, J=7.3 Hz, 1H), 6.44 (d, J=7.9 Hz, IH), 4.71 (q, J=6.8 Hz, 1H), 3.37 (q, J=18.0, 9.2 Hz, 1H), 3.27 (q, J=15.2, 8.4 Hz, 1H), 2.95 (s, 6H), 2.93 (t, J=8.0 Hz, 2H), 1.51 (d, J=6.9 Hz, 3H); $^{13}$C NMR (100 MHz, CDCl$_3$) ppm 128.2, 127.4, 124.8, 116.8, 112.6, 107.3, 92.1, 86.3, 53.9, 47.9, 41.0, 28.4, 16.3; HRMS (EI): Exact mass calcd for C$_{18}$H$_{22}$N$_2$ [M]$^+$, 266.1783. Found 266.1774.

EXAMPLE 5

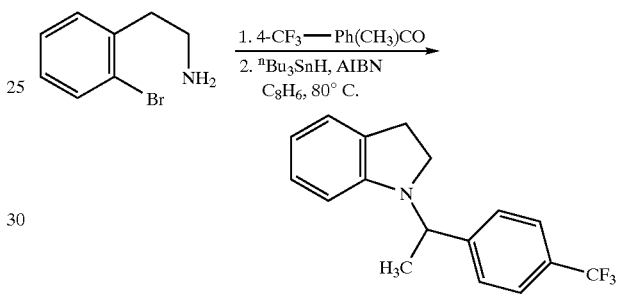

N-[(1-Methyl)-4-dimethylaminobenzyl]-indoline (2e).

Following the general procedure, o-bromophenethylamine (429 mg, 2.14 mimol), p-trifluoromethyl acetophenone (404 mg, 2.14 mmol), and 4 Å MS were stirred in benzene (5 mL) at room temperature for 4.5 h to provide the ketimine as a 93:7 mixture of stereoisomers. IR (film) 3064, 1636 cm$^{-1}$; $^1$H NMR (400 MHz, CDCl$_3$) δ 7.87 (d, J=8.2 Hz, 2H), 7.46 (d, J=8.3 Hz, 2H), 7.57 (d, J=7.8 Hz, 1H), 7.38 (s, 1H), 7.33–7.21 (m, 1H), 7.10 (t, J=7.7 Hz, 1H), 3.81 (t, J=7.3 Hz, 2H), 3.23 (t, J=7.3 Hz, 2H); $^{13}$C NMR (100 MHz, CDCl$_{13}$) ppm 164.9, 144.6, 139.8, 133.0, 131.7, 128.6, 128.7, 129.6, 127.6, 127.2, 125.6, 124.9, 52.3, 37.7, 15.7; HRMS (FAB): Exact mass calcd for C$_{17}$H$_{16}$BrF$_3$N [M+H]$^+$, 370.0418. Found 370.0428.

A three hour addition of a $^n$Bu$_3$SnH (91 μL, 337 μmol) and AIBN (20 mg, 123 μmol) solution in benzene (1 mL) to a refluxing solution of the unpurified ketimine (113 mg, 307 μmol) in benzene (31 mL) delivered, after flash chromatography (20% CH$_2$Cl$_2$ in hexanes), 65 mg (72%) of the desired indoline as a colorless oil; Rf=0.40 (10% EtOAchexanes; IR (film) 3048, 1606 cm$^{-1}$; 1H NMR (400 MHz, CDCl$_3$) δ 7.61 (d, J=8.3 Hz, 2H), 7.54 (d, J=8.3 Hz, 2H), 7.10 (d, J=6.9 Hz, 1H), 7.01 (t, J=7.5 Hz, 1H), 6.65 (t, J=7.1 Hz, 1H), 6.31 (d, J=7.9 Hz, 1H), 4.73 (q, J=6.8 Hz, 1H), 3.43 (dd, J=17.9, 8.7 Hz, 1H), 3.37 (dd, J=15.7, 7.4 Hz, 1H), 2.99 (t, J=8.3 Hz, 2H), 1.57 (d, J=6.9 Hz, 3H); $^{13}$C NMR (100 MHz, CDCl$_3$) ppm 151.3, 147.5, 130.4, 127.5, 127.4, 125.7, 125.6, 124.8, 54.9, 48.5, 28.5, 17.1; HRMS (EI): Exact mass calcd for C$_{17}$H$_{16}$F$_3$N [M]$^+$, 291.1235. Found 291.1234.

EXAMPLE 6

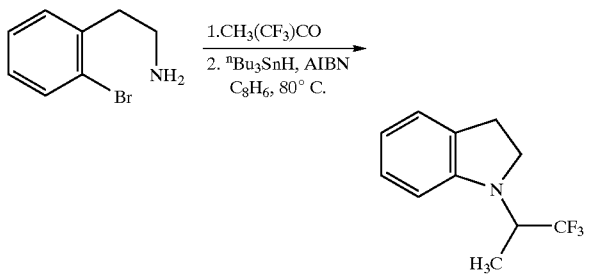

N-(1-Trifluoroethyl)-indoline (2i).

Following the general procedure, o-bromophenethylamine (200 mg, 999 tmol), trifluoroacetone (168 mg, 1.5 mmol), and 4 Å MS were stirred in benzene (5 mL) at room temperature for 4 h to provide the ketimine as a >95:5 mixture of stereoisomers. IR (film) 3059, 1686 cm$^{-1}$; $^1$H NMR (400 MHz, CDCl$_3$) δ 7.57 (d, J=8.3 Hz, 1H), 7.29–7.22 (m, 2H), 7.13 (dt, J=6.8, 2.4 Hz, 1H), 3.75 (t, J=7.3 Hz, 2H), 3.17 (t, J=7.3 Hz, 2H); 1.85 (s, 3H); $^{13}$C NMR (100 MHz, CDCl$_3$) ppm 157.3 (q, J=33.6 Hz), 138.6, 133.1, 131.8, 127.8, 124.7, 121.4, 118.6, 51.4, 36.6, 12.6; HRMS (EI): Exact mass calcd for C$_{11}$H$_{13}$BrF$_3$N [M+H]$^+$, 296.0086. Found 296.0088.

A three hour addition of a $^n$Bu$_3$SnH (133 μL, 495 μmol) and AIBN (30 mg, 180 μmol) solution in benzene (1 mL) to a refluxing solution of the unpurified ketimine (132 mg, 450 mol) in benzene (44 mL) provided, after flash chromatography (100% hexanes), 80 mg (83%) of the desired indoline as a colorless oil. Rf=0.15 (hexanes); IR (film) 3050, 1490 cm$^{-1}$; $^1$H NMR (400 MHz, CDCl$_3$) δ 7.07 (t, J=7.9 Hz, 2H), 6.65 (t, J=7.3 Hz, 1H), 6.44 (d, J=7.8 Hz, 1H), 4.14 (m, 1H), 3.54 (t, J=8.5 Hz, 2H), 3.03 (t, J=8.6 Hz, 2H), 1.38 (d, J=7.0 Hz, 3H); $^{13}$CNMR (100 MHz, CDCl$_3$) ppm 150.3, 129.3, 127.5, 125.0, 118.2, 114.0, 106.3, 52.8 (q,J=28.2 Hz), 47.1, 28.5, 10.5; HRMS (EI): Exact mass calcd for C$_{11}$H$_{12}$F$_3$N [M]$^+$, 215.0922. Found 215.0920.

EXAMPLE 7

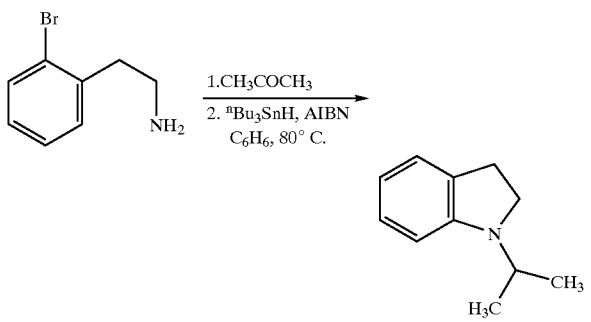

N-(iso-Propyl)-indoline (2g).

Following the general procedure, o-bromophenethylamine (150 mg, 750 Rmol), acetone (44 mg, 750 μmol) and 4 Å MS were stirred in benzene (5 μmL) at room temperature for 4 h to provide the ketimine. IR (film) 3055, 1653 cm$^{-1}$ $^1$H NMR (400 MHz, CDCl$_3$) δ 7.50 (d, J=8.3 Hz, 1H), 7.24–7.18 (m, 2H), 7.04 (td, J=6.9, 2.3 Hz, 1H), 3.46 (t, J=7.5 Hz, 2H), 3.06 (t, J=7.7 Hz, 2H), 1.99 (s, 3H), 1.71 (s, 3H); $^{13}$C NMR (100 MHz, CDCl$_3$) ppm 168.3, 139.9, 133.0, 131.4, 128.1, 127.6, 124.9, 51.6, 37.7, 29.5, 18.6; HRMS (EI) Calcd for C$_{11}$H$_{15}$BrN [MH]$^+$, 240.0310. Found 240.0389

A three-hour addition of $^n$Bu$_3$SnH (154 μL, 573 μmol) and AIBN (34 mg, 208 μmol) solution in benzene (1 mL) to a refluxing solution of the unpurified ketimine (125 mg, 521 μmol) in benzene (50 mL) delivered, after flash chromatography (30% CH$_2$Cl$_2$ Hexanes) 0.024 g (30%) of the desired indoline as a colorless oil. Rf=0.1 (30% CH$_2$Cl$_2$ Hexanes); IR (film) 3047, 1607 cm$^{-1}$; $^1$H NMR (400 MHz, CDCl$_3$) δ 7.04 (t, J=6.7 Hz, 2H), 6.59 (t, J=7.4 Hz, 1H), 6.42 (d, J=8.1 Hz, IH), 3.83 (sep, J=6.6 Hz, 1H), 3.33 (t, J=8.5 Hz, 2H), 2.93 (t, J=8.3 Hz, 2H), 1.15 (d, J=6.7 Hz, 6H); $^{13}$C NMR (100 MHz, CDCl$_3$) ppm 151.5, 130.5, 127.5, 124.6, 117.1, 107.3, 46.0, 45.7, 28.4, 18.4; HRMS (EI) Exact mass calcd for C$_{11}$H$_{15}$N [M]$^+$, 161.1204. Found 161.1201.

EXAMPLE 8

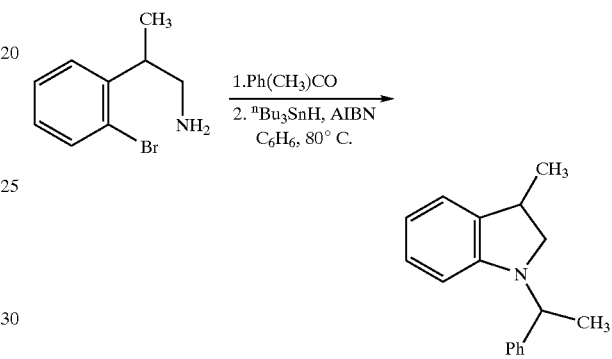

N-(1-Methylbenzyl)-3-methylindoline (5a).

Following the general procedure, 2-(o-bromophenyl)-2-methyl-ethylamine (353 mg, 1.65 mmol), acetophenone (192 μIL, 1.64 mmol), and 4 Å MS were stirred in toluene (5 mL) at room temperature for 12 h to provide the ketimine as a >95:5 mixture of stereoisomers. IR (film) 3057, 1633 cm$^{-1}$; $^1$H NMR (400 MHz, CDCl$_3$) δ 7.80 (m, 2H), 7.59 (d, J=6.9 Hz, 1H), 7.39 (m, 4H), 7.31 (t, J=6.9 Hz, 1H), 7.08 (t, J=6.1 Hz, 1H), 3.76 (dd, J=10.5, 6.3, Hz, 2H), 3.57 (dq, J=13.8, 6.9 Hz, 1H), 2.19 (s, 3H), 1.45 (d, J=6.7 Hz, 3H); $^{13}$C NMR (100 MHz, CDCl$_3$) ppm 165.5, 144.9, 141.4, 133.0, 129.6, 128.6, 128.4, 128.3, 127.8, 127.6, 126.8, 125.1, 58.1, 39.9, 18.8, 15.7; HRMS (EI): Exact mass calcd for C$_{17}$H$_{19}$BrN [M+H]$^+$, 316.0701. Found 316.0588.

A three hour addition of $^n$Bu$_3$SnH (84 μL, 314 μmol) and AIBN (18.7 mg, 114 μmol) benzene solution (1 mL) to a refluxing solution of the unpurified ketimine (90.3 mg, 286 μmol) in benzene (28 mL) afforded, after flash chromatography (1% ether in hexanes), 58.4 mg (86%) of the desired indoline as a yellow oil (58:42 mixture of diastereomers). Rf=0.6 (10% EtOAchexanes); IR (film) 3024, 1605 cm$^{-1}$; $^1$H NMR (400 MHz, CDCl$_3$) δ 7.43 (d, J=7.5 Hz, 4H), 7.35 (t, J=7.5 Hz, 6H), 7.03 (d, J=8.0 Hz, 2H), 7.01 (t, J=4.3 Hz, 2H), 6.65 (t, J=7.4 Hz, 2H), 6.36 (d, J=4.3 Hz, 2H), 4.74 (q, J=6.9 Hz, 1H), 4.68 (q, J=6.8 Hz, 1H), 3.62 (dd, J=8.8, 8.8 Hz, 1H), 3.45 (dd, J=8.6, 8.6 Hz, 1H), 3.30 (dq, J=14.6, 7.3 Hz, 1H), 2.95 (dd, J=8.8, 8.8 Hz, 2H), 1.57 (d, J=7.0 Hz, 3H), 1.52 (d, J=6.9 Hz, 3H), 1.33 (d, J=6.7 Hz, 3H), 1.27 (d, J=6.8 Hz, 3H); $^{13}$C NMR (100 MHz, CDCl$_3$) ppm 151.5, 150.8, 146.4, 143.5, 142.8, 135.4, 135.3, 128.68, 128.62, 127.57, 127.53, 127.2, 127.1, 123.5, 123.1, 117.3, 117.0, 107.5, 107.2, 56.5, 56.0, 54.9, 54.3, 35.0, 19.9, 18.3, 17.2, 16.5; HRMS (EI): Exact mass calcd for C$_{17}$H$_{19}$N [M]$^+$, 237.1517. Found 237.1509.

EXAMPLE 9

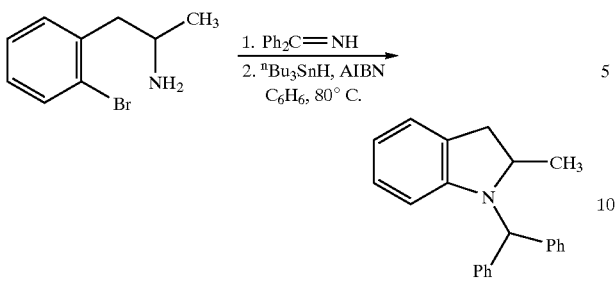

N-(1-Phenylbenzyl)-2-methylindoline (5b).

Following the general procedure, 2-(o-bromophenyl)-1-methylethylamine (50 mg, 234 μmol), benzophenone imine (42 mg, 233 μmol) and 4 Å MS were stirred in dichloromethane (2.5 mL) at room temperature for 3 days under argon atmosphere to provide the ketimine as a solid (mp 59–61° C.); IR (film) 3057, 1726, 1661 cm$^{-1}$; $^1$H NMR (400 MHz, CDCl$_3$) δ 7.59 (d, J=6.9 Hz, 2H), 7.45 (d, J=7.4 Hz, 1H), 7.37–7.30 (m, 6H), 7.20–7.14 (m, 2H), 7.03 (dt, J=6.9, 1.4 Hz, 1H), 6.63 (d, J=6.7 Hz, 2H), 3.81 (qd, J=7.8, 6.2, Hz, 1H), 3.03 (d, J=4.5 Hz, 1H), 3.01 (d, J=7.1 Hz, 1H), 1.30 (d, J=6.2 Hz, 3H); $^{13}$C NMR (100 MHz, CDCl$_3$) ppm 167.1, 140.2, 139.4, 137.3, 132.6, 130.3, 129.9, 128.6, 128.4, 128.2, 128.1, 127.8, 127.6, 127.1, 125.4, 57.4, 44.8, 22.4; HRMS (EI): Exact mass calcd for C$_{22}$H$_{20}$BrN [M]$^+$, 377.0779. Found 377.0630.

To a refluxing solution of the unpurified ketimine (20 mg, 53 μmol) in benzene (9 mL) was added $^n$Bu$_3$SnH (15.6 μL, 58.2 μmol), followed by a four-hour addition of AIBN (10.4 mg, 63.5 tmol) dissolved in benzene (2 mL). After the first 2 h of the reaction, another lot of $^n$Bu$_3$SnH (15.6 μL, 58.2 μmol) was added to the reaction mixture. After the complete addition of AIBN, the reaction mixture was refluxed for 1 h, followed by removal of solvent. Flash chromatography (5% CH$_2$Cl$_2$ in hexanes) yielded the desired indoline (13.1 mg, 78%) as a solid (mp 58–61° C.); IR (film) 3060, 1635 cm$^{-1}$; 1H NMR (400 MHz, CDCl$_3$) δ 7.41 (d, J=7.6 Hz, 2H), 7.37–7.26 (m, 8H), 7.04 (d, J=7.1 Hz, 1H), 6.82 (t, J=7.5 Hz, 11H), 6.59 (t, J=7.3 Hz, 1H), 5.97 (d, J=7.9 Hz, 1H), 5.65 (s, 1H), 3.83 (qd, J=15.0, 6.2 Hz, 1H), 3.25 (dd, J=15.6, 9.0 Hz, 1H), 2.65 (dd, J=15.4, 6.9 Hz, 1H), 1.16 (d, J=6.0 Hz, 3H); $^{13}$C NMR (75 MHz, CDCl$_3$) ppm 138.9, 129.2, 129.0, 128.8, 127.6, 127.2, 124.7, 117.4, 109.4, 100.4, 65.5, 52.0, 37.6, 30.1, 21.0; HRMS (EI): Exact mass calcd for C$_{22}$H$_{21}$N [M]$^+$, 299.1674. Found 299.1682.

EXAMPLE 10

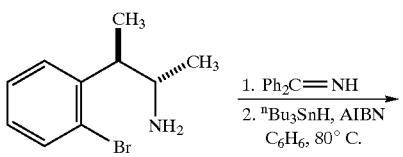

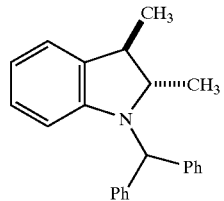

N-(1-Phenylbenzyl)-2,3-trans-dimethylindoline (5c).

Following the general procedure, 2-(o-bromophenyl)-1,2-cis-dimethylethylamine (127 mg, 562 μmol), benzophenone imine (102 mg, 562 lmol), and 4 Å MS were stirred in dichloromethane (1.5 mL) at room temperature for 7.5 days under argon atmosphere to provide the ketimine as an oil; IR (film) 3079, 1661 cm$^{-1}$; $^1$H NMR (400 MHz, CDCl$_3$) δ 7.52–7.48 (m, 3H), 7.44–7.40 (m, 3H), 7.34–7.27 (m, 3H), 7.19 (q, J=7 Hz, 1H), 7.18–7.16 (m, 1H), 7.00–6.95 (m, 3H), 3.64 (q, J=6.3 Hz, 2H), 3.62 (q, J=6.3 Hz, 1H), 1.44 (d, J=6.6 Hz, 3H), 1.41 (d, J=6.2 Hz, 3H); $^{13}$C NMR (100 MHz, CDCl$_3$) ppm 144.6, 140.6, 137.3, 132.7, 129.8, 129.6, 128.7, 128.4, 128.1, 127.5, 62.4, 53.6, 44.8, 19.7, 17.7; HRMS (EI): Exact mass calcd for C$_{23}$H$_{23}$BrN [M+H]$^+$, 392.1016. Found 392.0913.

To a refluxing solution of the unpurified ketimine (12.6 mg, 32 μmol) in benzene (5.5 mL) was added $^n$Bu$_3$SnH (9.5 μL, 35 μmol), followed by a 6 h addition of AIBN (13 mg, 80 μmol) dissolved in benzene (1 mL). After the first 3 h of the reaction, another aliquot of $^n$Bu$_3$SnH (9.5 μL, 35.4 μmol) was added. After complete addition of AIBN, the reaction mixture was refluxed for further 1 h followed by evaporation of solvent under vacuum. Flash chromatography (5% CH$_2$Cl$_2$ in hexanes) yielded the desired indoline (7.9 mg, 79%) as a gum; IR (film) 2958, 1684 cm$^{-1}$; $^1$H NMR (400 MHz, CDCl$_3$) δ 7.39 (d, J=7.2 Hz, 2H), 7.35–7.26 (m, 8H), 7.02 (d, J=7.2 Hz, 1H), 6.83 (t, J=7.6 Hz, 1H), 6.61 (t, J=7.3 Hz, 1H), 5.99 (d, J=7.9 Hz, 1H), 5.69 (s, 1H), 3.28 (dq, J=6.3, 6.3 Hz, 1H), 2.87 (dq, J=6.9, 6.9 Hz, 1H), 1.27 (d, J=6.4 Hz, 3H), 1.19 (d, J=6.2 Hz, 3H); $^{13}$C NMR (100 MHz, CDCl3) ppm 150.4, 141.1, 140.5, 134.3, 128.9, 128.6, 127.4, 123.2, 117.2, 109.2, 66.5, 65.0, 43.8, 20.0, 18.8; HRMS (EI): Exact mass calcd for C$_{23}$H$_{23}$N [M]$^+$, 313.1830. Found 313.1838. Relative stereochemistry assigned by NOE experiments (400 MHz NMR).

EXAMPLE 11

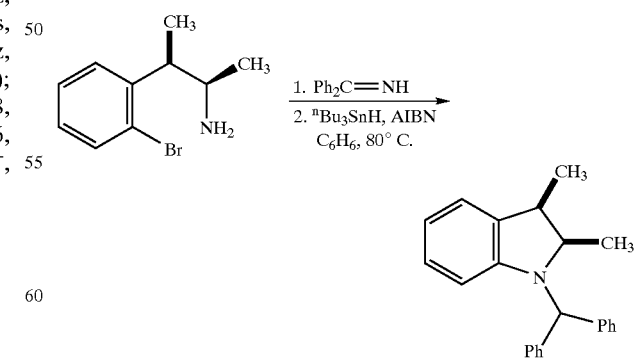

N-(1-Phenylbenzyl)-2,3-cis-dimethylindoline (5d).

Following the general procedure, 2-(o-bromophenyl)-1,2-trans-dimethylethylamine (18 mg, 79.7 μmol), benzophenone imine (14.4 mg, 79.7 μmol) and 4 Å MS were stirred in dichloromethane (1 mL) at room temperature for 7.5 days under argon atmosphere to provide the ketimine as an oil; IR (film) 3059, 1624 cm$^{-1}$; $^1$H NMR (400 MHz, CDCl$_3$) δ 7.83 (d, J=7.1 Hz, 2H), 7.62 (dt, J=7.4, 1.2 Hz, 2H), 7.51 (t, J=7.7 Hz, 3H), 7.39–7.32 (m, 4H), 7.16 (t, J=7.3 Hz, 1H), 7.03 (t, J=7.7 Hz, IH), 6.80–6.79 (m, 1H), 3.61 (q, J=6.2 Hz, 1H), 3.54 (q, J=6.7 Hz, 1H), 1.33 (d, J=7.0 Hz, 3H), 1.13 (d, J=6.3 Hz, 3H); $^{13}$C NMR (100 MHz, CDCl$_3$) ppm 137.2, 132.9, 132.7, 130.3, 129.9, 128.99, 128.5, 128.3, 127.6, 127.3, 61.4, 29.9, 20.6, 16.7; HRMS (EI): Exact mass calcd for C$_{23}$H$_{22}$BrN [M+H]$^+$, 392.1016. Found 392.1160.

To a refluxing solution of the unpurified ketimine (5.1 mg, 13 μmol) in benzene (3 mL) was added $^n$Bu$_3$SnH (4.6 μL, 16.9 μmol), followed by a 6 h addition of AIBN (6.4 mg, 39.0 1 mol) dissolved in benzene (1 mL). After the first 3 h of reaction, another aliquot of $^n$Bu$_3$SnH (4.6 μL, 16.9 μmol), was added to the reaction mixture. After the complete addition of AIBN, the reaction mixture was refluxed for a further 2 h, followed by evaporation of solvent under vacuum. Flash chromatography (5% CH$_2$Cl$_2$ in hexanes) yielded the desired product (3.4 mg, 84%) as a gum; IR (film) 3061, 1605 cm$^{-1}$; $^1$H NMR (400 MHz, CDCl$_3$) δ 7.45 (d, J=6.8 Hz, 2H), 7.40 (d, J=7.2 Hz, 2H), 7.34–7.23 (m, 6H), 7.03 (d, J=7.1 Hz, 1H), 6.80 (t, J=7.5 Hz, 1H), 6.63 (t, J=7.3 Hz, 1H), 5.90 (d, J=7.8 Hz, 1H), 5.51 (s, 1H), 3.78 (dq, J=7.5, 6.4 Hz, 1H), 3.38 (dq, J=7.3, 7.3 Hz, 1H), 1.22 (d, J=7.1 Hz, 3H), 0.95 (d, J=6.3 Hz, 3H); $^{13}$C NMR (100 MHz, CDCl$_3$) ppm 150.0, 142.4, 141.2, 135.5, 128.9, 128.7, 128.6, 127.9, 127.4, 127.2, 126.9, 123.1, 117.5, 109.9, 65.4, 62.4, 39.1, 13.6, 12.6; HRMS (FAB): Exact mass calcd for C$_{23}$H$_{23}$N [M]$^+$, 313.1830. Found 313.1839.
Relative Stereochemistry Determined by NOE Experiments (400 MHz NMR).

EXAMPLE 12

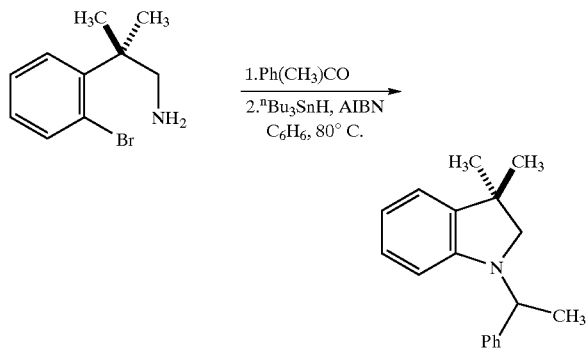

N-(1-Methylbenzyl)-3,3-dimethylindoline (5e).

According to the general procedure, 2-(o-bromophenyl)-2,2-dimethyl ethylamine (733 mg, 3.21 mmol), acetophenone (370 μL, 3.18 mmol), and 4 Å MS were stirred in toluene (25 mL) at room temperature for 12 h to provide the ketimine as a >95:5 mixture of stereoisomers, IR (film) 3058, 1635 cm$^{-1}$; $^1$H NMR (400 MHz, CDCl$_3$) δ 7.66 (m, 2H), 7.55 (d, J=9.1 Hz, IH), 7.50 (d, J=9.8 Hz, 1H), 7.30 (t, J=1.8 Hz, 3H), 7.23 (t, J=4.3 Hz, 1H), 7.0 (t, J=9.4 Hz, 1H), 3.98 (s, 2H), 2.20 (s, 3H), 1.64 (s, 6H); $^{13}$C NMR (100 MHz, CDCl$_3$) ppm 164.3, 146.3, 141.5, 135.8, 130.0, 129.4, 128.2, 127.7, 127.3, 126.8, 122.8, 60.4, 41.8, 26.8, 26.5, 15.6; HRMS (CI): Exact mass calcd for C$_{18}$H$_{21}$BrN, [M+H]$^+$, 330.0857. Found 330.0818.

A three hour addition of $^n$Bu$_3$SnH (72.0 μL, 267 μmol) and AIBN 16 mg, 97 μmol) benzene solution (1.0 mL) to a refluxing solution of the unpurified ketimine (80.2 mg, 243 μmol) in benzene (24 mL) furnished, after flash chromatography (1% Et$_2$O in hexanes) 48.8 mg (80%) of the desired indoline as a colorless oil. Rf=0.63 (10% EtOAchexanes); IR (film) 3024, 1604 cm$^{-1}$; $^1$H NMR (400 MHz, CDC$_{13}$) δ 7.41 (d, J=7.4 Hz, 2H), 7.35 (t, J=7.2 Hz, 2H), 7.26 (d, J=7.3 Hz, 1H), 7.01 (t, J=7.2 Hz, 1H), 7.01 (t, J=7.2 Hz, 1H), 6.66 (t, J=8.1 Hz, 1H), 6.35 (d, J=8.1 Hz, 1H), 4.73 (q, J=6.9 Hz, 1H), 3.18 (d, J=8.3 Hz, 1H), 3.08 (d, J=8.3 Hz, 1H), 1.54 (d, J=6.9 Hz, 3H), 1.33 (s, 3H), 1.27 (s, 3H); $^{13}$C NMR (100 MHz, CDCl$_3$) ppm 150.1, 143.4, 139.2, 128.6, 127.5, 127.2, 127.1, 121.8, 117.2, 107.3, 62.6, 54.3, 39.9, 28.3, 27.4, 17.0; HRMS (EI): Exact mass calcd for C$_{18}$H$_{21}$N [M]$^+$, 251.1674. Found 251.1672.

EXAMPLE 13

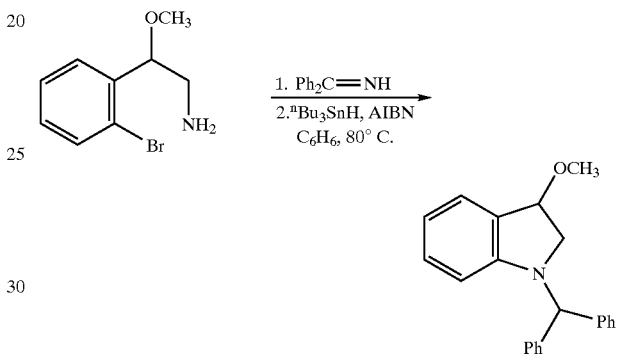

N-(1-Phenylbenzyl)-3-methoxyindoline (5f).

2-(o-Bromophenyl)-2-methoxyethylamine (43.4 mg, 189 μmol), benzophenone imine (32 μL, 189 μmol), and 4 Å MS were stirred in CH$_2$Cl$_2$ at room temperature for 7 h. Removal of the solvent provided the ketimine as a colorless oil. IR (film) 3058, 1626 cm$^{-1}$; $^1$H NMR (400 MHz, CDCl$_3$) δ 7.63 (d, J=8.3 Hz, 2H), 7.52 (dd, J=8.1, 2.2 Hz, 1H), 7.45–7.28 (m, 8H), 7.13 (dt, J=9.3, 1.6 Hz, 1H), 7.07 (dd, J=7.5, 2.4 Hz, 2H), 5.05 (dd, J=6.7, 4.5 Hz, 1H), 3.71 (dd, J=14.0, 4.4 Hz, 1H), 3.64 (dd, J=14.0, 6.9 Hz, 1H), 3.36 (s, 3H); $^{13}$C NMR (100 MHz, CDCl$_3$) ppm 169.8, 140.1 (2C), 137.0, 132.82, 130.2, 129.1, 128.8 (2C), 128.65, 128.6, 128.54, 128.2, 127.7, 123.8, 82.8, 59.2, 57.6; HRMS (EI): Exact mass calcd for C$_{22}$H$_{21}$BrNO [M+H]$^+$, 394.0808. Found 394.0795.

A three hour addition of $^n$Bu$_3$SnH (38 μL, 143 μmol) and AIBN (8.5 mg, 52 μmol) in benzene (1 mL) to a refluxing solution of the unpurified ketimine (51.2 mg, 130 μmol) in benzene (13 mL) afforded, after flash chromatography on basic alumina (10% CH$_2$Cl$_2$ in hexanes), 29 mg (70%) of the desired indoline as a colorless oil. Rf=0.15 (10% CH$_2$Cl$_2$ hexanes); IR (film) 3059, 1608 cm$^{-1}$; $^1$H NMR (400 MHz, CDCl$_3$) δ 7.40–7.26 (m, 11H), 7.10 (dt, J=8.1, 1.2 Hz, 1H), 6.71 (t, J=7.25 Hz, 1H), 6.34 (d, J=7.9 Hz, 1H), 5.70 (s, 1H), 4.79 (dd, J=6.7, 2.6 Hz, 1H), 3.35 (s, 3H), 3.33 (dd, J=11.3, 2.7 Hz, 1H), 3.27 (dd, J=11.2, 6.7 Hz, 1H); $^{13}$C NMR (100 MHz, CDCl$_3$) ppm 140.7, 130.1, 129.2, 128.8, 128.7, 128.4, 128.2, 127.7, 127.5, 126.1 78.9, 65.7, 56.4, 55.4; HRMS (EI): Exact mass calcd for $C_{22}H_{21}NO$ [M]$^+$, 315.1623. Found 315.1623.

EXAMPLE 14

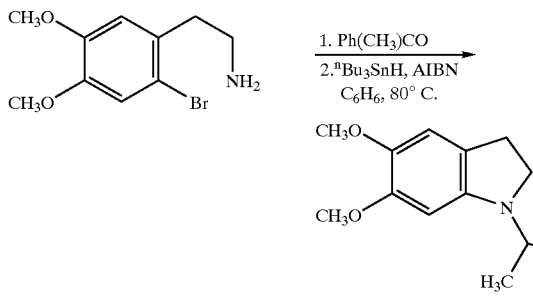

N-(1-Methylbenzyl)-5,6-dimethoxy indoline (8a).

Following the general procedure, (2-bromo-4,5-dimethoxyphenyl)ethylamine (1.95 g, 7.5 mmol), acetophenone (0.87 mL, 7.5 mmol), and 4 Å MS were stirred in toluene (10 mL) at room temperature for 12 h to provide the ketimine as a >95:5 mixture of stereoisomers. IR (film) 3055, 1633 cm$^{-1}$; $^1$H NMR (400 MHz, CDCl$_3$) δ 7.77 (m, 2H), 7.38 (m, 3H), 7.03 (s, 1H), 6.83 (s, 1H), 3.87 (s, 3H), 3.79 (s, 3H), 3.77 (dd, J=7.2, 7.2 Hz, 2H), 3.14 (dd, J=7.4, 7.4 Hz, 2H), 2.11 (s, 3H); $^{13}$C NMR (100 MHz, CDCl$_3$) ppm 166.1, 158.0, 148.3, 148.2, 141.4, 131.9, 129.7, 128.5, 126.7, 115.6, 114.4, 56.3, 56.1, 52.2, 37.3, 15.6; HRMS (CI): Exact mass calcd for $C_{18}H_{21}BrNO_2$ [MH]$^+$, 362.0756. Found 362.0747.

A three-hour addition of $^n$Bu$_3$SnH (120 μL), 448 μmol) and AIBM (26.7 mg, 163 μmol) solution in benzene (1.1 mL) to a refluxing solution of the unpurified ketimine (148 mg, 408 μmol) in benzene (41 mL) afforded, after flash chromatography (15% EtOAc in hexanes), 95.6 mg (83%) of the desired indoline as a yellow oil. Rf=0.27 (20% EtOAchexanes); IR (film) 3059, 1614 cm$^{-1}$; $^1$H NMR (400 MHz, CDCl$_3$) δ 7.45 (d, J=7.6 Hz, 2H), 7.36 (t, J=7.6 Hz, 2H), 7.27 (t, J=7.4 Hz, 1H), 6.75 (s, 1H), 6.00 (s, 1H), 4.57 (q, J=6.8 Hz, 1H), 3.80 (s, 3H), 3.70 (s, 3H), 3.34 (dd, J=16.2, 7.3 Hz, 2H), 2.88 (dd, J=7.9, 7.9 Hz, 2H), 1.53 (d, J=7.0 Hz, 3H); $^{13}$C NMR (100 MHz, CDCl$_3$) ppm 149.0, 146.5, 143.6, 141.5, 128.6, 127.3, 127.1, 121.3, 111.2,95.4, 57.6,49.6,28.4, 17.5; HRMS (EI): Exact mass calcd for $C_{18}H_{21}NO_2$ [M]$^+$, 283.1572. Found 283.1578.

EXAMPLE 15

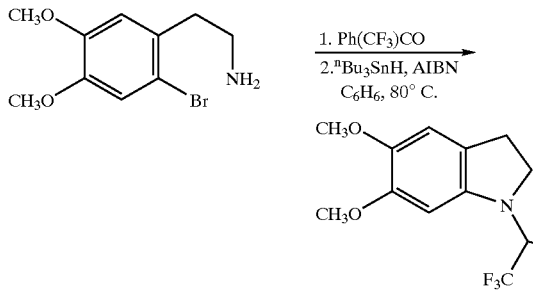

N-(1-Trifluoromethyl(benzyl)-5,6-dimethoxy indoline (8b).

Following the general procedure, (2-bromo-4,5-dimethoxy-phenyl)ethylamine (2.05 g, 7.88 mmol), trifluoroacetophenone (1.1 μL, 7.88 mmol), and 4A MS were stirred in toluene (30 mL) at room temperature for 12 h to give the ketimine as a >95:5 mixture of stereoisomers. IR (film) 3061, 1669 cm$^{-1}$; $^1$H NMR (400 MHz, CDCl$_3$) δ 7.43 (t, J=7.2 Hz, 1H), 7.38 (t, J=7.5 Hz, 2H), 6.95 (s, 1H), 6.91 (d, J=7.1 Hz, 2H), 6.70 (s, 1H), 3.87 (s, 3H), 3.84 (s, 3H), 3.67 (dd, J=8.2, 6.8 Hz, 2H), 3.05 (dd, J=6.7, 6.7 Hz, 2H); $^{13}$C NMR (100 MHz, CDCl$_3$) ppm 159.5, 159.2, 148.5, 148.3, 130.4, 130.2, 130.1, 128.8, 128.5, 127.7, 121.1, 118.4, 115.5, 114.5, 114.2, 56.4, 56.1, 52.9, 36.4; HRMS (EI): Exact mass calcd for $C_{18}H_{17}BrF_3NO_2$ [M]$^+$, 415.0395. Found 415.0414.

A three-hour addition of $^n$Bu$_3$SnH (110 μL, 412 μmol) and AIBN (25 mg, 150 μmol) solution in benzene 1.0 mL) to a refluxing solution of the unpurified ketimine (156 mg, 375 μmol) in benzene (37 mL) provided, after flash chromatography (10% EtOAc in hexanes), 113 mg (89%) of the desired indoline as a yellow oil. Rf=0.37 (20% EtOAchexanes); IR (film) 2939, 1615 cm$^{-1}$; $^1$H NMR (400 MHz, CDC13) δ 7.39 (m, 5H), 6.74 (s, 1H), 6.27 (s, 1H), 5.11 (q, J=8.6 Hz, 1H), 3.87 (s, 3H), 3.81 (s, 3H), 3.57 (dd, J=15.1, 8.8 Hz, 1H), 3.15 (dd, J=18.4, 9.3 Hz, 1H), 2.89 (m, 2H); $^{13}$C NMR (100 MHz, CDC13) ppm 149.3, 144.9, 142.4, 132.0, 128.9, 120.2, 111.2,94.2,62.8 (q,J=29.7Hz, 1C), 57.4,56.6,49.6, 28.5; HRMS (EI): Exact mass calcd for $C_{18}H_{18}F_3NO_2$ [M]$^+$, 337.1290. Found 337.1280.

EXAMPLE 16

N-(1-Phenylbenzyl)-5,6-dimethoxy indoline (8c).

Following the general procedure, (2-bromo-4,5-dimethoxyphenyl)ethyl amine (343 mg, 1.32 mmol) and benzophenone imine (239 mg, 1.32 mmol) were stirred at room temperature in CH$_2$Cl$_2$ (3 mL) for 12 h to give the ketimine. IR (film) 3056, 1623 cm$^{-1}$; $^1$H NMR (400 MHz, CDCl$_3$) δ 7.62 (d, J=7.0 Hz, 2H), 7.40 (dd, J=6.2,3.4 Hz, 3H), 7.36 (t, J=7.6 Hz, 3H), 6.95 (s, 1H), 6.94 (d, J=2.3 Hz, 2H), 6.73 (s, 1H), 3.84 (s, 3H), 3.76 (s, 3H), 3.67 (dd, J=7.0, 7.0 Hz, 2H), 3.07 (dd, J=7.2, 7.2 Hz, 2H); $^{13}$C NMR (100 MHz, CDCl$_3$) ppm 168.9, 148.2, 139.9, 136.8, 131.8, 128.5, 128.4, 128.3, 127.9, 115.5, 114.5, 114.2, 56.3, 56.1, 53.8, 37.4; HRMS (CI): Exact mass calcd for $C_{23}H_{23}BrNO_2$ [M+H]$^+$, 424.0912. Found 424.0910.

A three-hour addition of $^n$Bu$_3$SnH (75 μL, 278 μmol) and AIBN (17 mg, 101 μmol) solution in benzene (1.0 mL) to refluxing solution of the unpurified ketimine (107 mg, 252 pimol) in benzene (25 mL) provided, after flash chromatography (5% EtOAc in hexanes), 46 mg (64%) of the desired indoline as a white solid. mp 105–106° C.; Rf=0.20 (10% EtOAchexanes); IR (film) 2931, 1597 cm$^{-1}$; $^1$H NMR (400 MHz, CDCl$_3$) δ 7.45 (d, J=7.1 Hz, 4H), 7.35 (t, J=7.1 Hz, 4H), 7.27 (t, J=4.7 Hz, 2H), 6.75 (s, 1H), 5.79 (s, 1H), 5.33 (s, 1H), 3.80 (s, 3H), 3.51 (s, 3H), 3.16 (dd, J=8.3, 8.3, Hz, 2H), 2.87 (dd, J=8.1, 8.1, Hz, 2H); $^{13}$C NMR (100 MHZ, CDCl$_3$) ppm 148.4, 146.9, 142.1, 141.8, 128.7, 128.5, 127.4, 121.7, 110.4, 96.5, 69.3, 57.3, 55.9, 53.6, 28.5; HRMS (CI): Exact mass caled for $C_{23}H_{23}NO_2$ [M]$^+$, 345.1729. Found 345.1713.

EXAMPLE 17

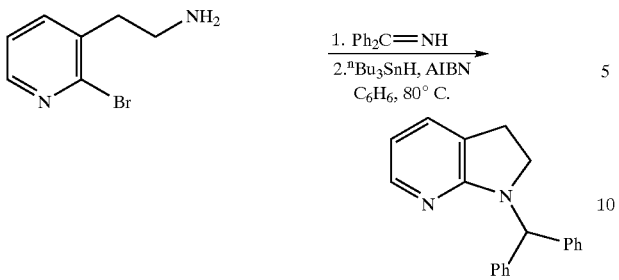

N-(1-Phenylbenzyl)-6-azaindoline (8d).

2-Bromo-3-(2-aminoethyl) pyridine (104 mg, 517 μmol) and benzophenone imine (94 mg, 517 μmol) were stirred in $CH_2Cl_2$ at room temperature for 8 h to provide the ketimine. IR (film) 3056, 1622 $cm^{-1}$; $^1H$ NMR (400 MHz, $CDCl_3$) δ 8.20 (dd, J=4.7, 0.9 Hz, 1H), 7.56 (t, J=7.8 Hz, 3H), 7.43–7.40 (m, 3H), 7.37 (d, JJ=6.6 Hz, 1H), 7.32 (t, J=7.9 Hz, 2H), 7.16 (dd, J=7.4, 5.2 Hz, 1H); 6.96 (t, J=3.4 Hz, 2H), 3.69 (t, J=6.9 Hz, 2H), 3.10 (t, J=6.9 Hz, 2H); $^{13}C$ NMR (100 MHz, $CDCl_3$) ppm 169.2, 158.1, 147.7, 144.5, 139.5, 137.0, 136.5, 130.0, 128.5, 128.4, 128.3, 127.5, 122.6, 52.4, 36.8; HRMS (EI): Exact mass calcd for $C_{20}H_{17}BrN_2$ $[M]^+$, 364.0575. Found 364.0587.

A two-hour addition of $^nBu_3SnH$ (58 μL, 214 μmol) and AIBN (39 mg, 235 μmol) solution in benzene (2 mL) to a refluxing solution of the unpurified ketimine (36 mg, 98 μmol) in benzene (10 mL) delivered, after flash chromatography (5% EtOAcHexanes), 14 mg (50%) of the desired indoline as an orange crystalline solid. mp 101° C.; Rf=0.1 (5% EtOAcHexanes); IR (film) 3058, 1611 $cm^{-1}$; $^1H$ NMR (400 MHz, $CDCl_3$) δ 7.87 (d, J=5.2 Hz, 1H), 7.34–7.26 (m, 10H), 7.17 (d, J=7.0 Hz, 1H), 6.81 (s, 1H), 6.42 (t, J=6.5Hz, 1H), 3.34 (t, J=8.5Hz, 2H), 2.97 (t, J=8.5 Hz, 2H); $^{13}C$ NMR (100 MHz, $CDCl_3$) ppm 162.8, 146.1, 140.2, 131.2, 122.8, 129.1, 128.5, 127.4, 112.4, 60.0, 45.6, 25.9; HRMS (EI) Calcd for $C_{20}H_{18}N_2$ $[M]^+$, 286.1470. Found 286.1468.

EXAMPLE 33

General Example for Vinyl Amination

4-Pentyn-1-amine (0.59 g) was dissolved in 8 mL of dry benzene, and 4 Å molecular sieves (~4 g) were added to the solution. The mixture was stirred at room temperature and 0.78 mL of acetophenone was added dropwise. The mixture was allowed to stirr for at least 6 hours. The reaction mixture was filtered through a plug of celite, and the molecular sieves were washed with ether. The solvent was washed in vacuo to afford the 4-pentyn-1-imine in 94% yield.

The imine (0.1709 g) was dissolved in 46 mL benzene and heated to reflux at 85°. AIBN (0.0224 g, 0.2 eq.) and tri-n-butyltin hydride (0.25 mL, eq.) were dissolved in a minimal amount of benzene (~1 mL) and drawn into syringe. This solution was added dropwise over 3 hours via syringe pump to the refluxing imine solution. After complete addition of AIBN and tri-n-butyltin hydride, the mixture was allowed to reflux for an additional 3 hours. Once the reaction had gone to completion, the reaction mixture was cooled to room temperature and the solvent was removed in vacuo.

We claim:
1. A free radical intermediate of the formula

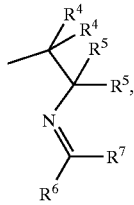

wherein said fused aryl and/or heterocyclic ring comprises
a $C_6$–$C_{14}$ N aryl group;
a 5 to 7 membered saturated monocyclic ring comprising carbon atoms and 1 to 4 heteroatoms selected from the group consisting of N, O, and S;
a 5 to 7 membered partially saturated monocyclic ring comprising carbon atoms and 1 to 4 heteroatoms selected from the group consisting of N, O, and S;
a 5 to 7 membered aromatic ring comprising carbon atoms and 1 to 4 heteroatoms selected from the group consisting of N, O, and S;
a 7 to 10 membered saturated bicyclic heterocyclic ring comprising carbon atoms and 1 to 4 heteroatoms selected from the group consisting of N, O, and S;
a 7 to 10 membered partially saturated bicyclic heterocyclic ring comprising carbon atoms and 1 to 4 heteroatoms selected from the group consisting of N, O, and S; or
a 7 to 10 membered aromatic bicyclic heterocyclic ring comprising carbon atoms and 1 to 4 heteroatoms selected from the group consisting of N, O, and S; and
said fused aryl and/or heterocyclic ring possesses an $sp^2$ hybridized carbon radical alpha to its point of attachment, and wherein each of the groups $R^4$, $R^5$, and $R^8$ are independently selected from hydrogen, aryl; heteroaryl; hydrocarbyl; substituted aryl; substituted heteroaryl; substituted hydrocarbyl; heteratom connected aryl; heteroatom connected hydrocarbyl; heteroatom connected substituted hydrocarbyl; heteroatom connected heteroaryl; heteroatom connected substituted aryl; halo; amino; cyano; hydroxy; carboxy; a group of the formula —C(O)O—$C_1$–$C_8$ alkyl; a group of the formula —C(O)$R^1$; a group of the formula —O—$R^1$; a group of the formula —NH$R^1$; a group of the formula —N($R^1$)$_2$; $C_1$–$C_8$ alkoxy; $C_1$–$C_8$ alkylthio; or two of $R^5$ and $R^6$, or two $R^8$ groups taken together can form a divalent hydrocarbyl, substituted hydrocarbyl, or be bonded directly to a heteroatom selected from oxygen, nitrogen, or sulfur; and n is a number equivalent to available sites on said aryl and/or heterocyclic ring;
in addition, two $R^4$ groups and/or two $R^5$ groups can be taken together represent oxo;
$R^1$ is selected from the group consisting of aryl, heteroaryl, hydrocarbyl, substituted aryl, substituted heteroaryl, and substituted hydrocarbyl; provided that $R^1$ is bonded via a carbon atom; and
$R^6$ and $R^7$ are independently selected from aryl, heteroaryl, hydrocarbyl, substituted aryl, substituted heteroaryl, and substituted hydrocarbyl; provided that said groups are bonded via a carbon atom.

2. The free radical intermediate of claim 1, wherein the fused aryl and/or heterocyclic ring comprises a pyridyl group; $R^4$, $R^5$, and $R^8$ comprise hydrogen; and $R^6$ and $R^7$ comprise phenyl.

\* \* \* \* \*